United States Patent [19]
Nicola et al.

[11] Patent Number: 6,136,957
[45] Date of Patent: Oct. 24, 2000

[54] ANTIBODIES WHICH BIND GRANULOCYTE-MACROPHANE COLONY-STIMULATING FACTOR RECEPTOR

[75] Inventors: Nicos Anthony Nicola; Nicholas Martin Gough, both of Melbourne, Australia; David Paul Gearing, Wellesley, Mass.; Donald Metcalf, Melbourne, Australia; Julie Ann King, Wellesley, Mass.

[73] Assignee: Amrad Corporation Limited, Victoria, Australia

[21] Appl. No.: 08/895,474

[22] Filed: Jul. 16, 1997

Related U.S. Application Data

[63] Continuation of application No. 08/384,828, Feb. 7, 1995, Pat. No. 5,726,036, which is a continuation of application No. 08/351,149, Nov. 23, 1994, Pat. No. 5,629,283, which is a continuation of application No. 07/834,534, Nov. 10, 1992, abandoned, which is a division of application No. PCT/AU90/00342, Aug. 10, 1990.

[30] Foreign Application Priority Data

Aug. 11, 1989 [AU] Australia ................................. PJ5743
May 8, 1990 [AU] Australia ................................. PK0014

[51] Int. Cl.[7] .................................................. C07K 16/28
[52] U.S. Cl. .................................... 530/387.9; 530/388.22
[58] Field of Search ............................. 530/388.22, 387.9

[56] References Cited

U.S. PATENT DOCUMENTS 5,112,961  5/1992  Hayashida et al. ....................... 536/27

OTHER PUBLICATIONS

Baldwin, G.C. et al., "Identification and Characterization of a Low–Affinity Granulocyte–Macrophage Colony–Stimulating Factor Receptor on Primary and Cultured Human Melanoma Cells," *Blood* 78(3):609–615 (Aug. 1991).

DiPersio, J.F. et al., "Characterization of the Human Granulocyte–Maccrophage Colony–stimulating Factor Receptor," *J. Biol. Chem.* 263(4):1834–1841 (Feb. 1988).

DiPersio, J.F. et al., "Human Granulocyte–Macrophage Colony–Stimulating Factor and Other Cytokines Prime Human Neutrophils for Enhanced Arachidonic Acid Release and Leukotriene $B_4$ Synthesis," *J. Immunol.* 140:4315–4322 (Jun. 1988).

DiPersio, J.F. et al., "Characterization of the Soluble Human Granulocyte–Macrophage Colony–Stimulating Factor Receptor Complex," *J. Biol. Chem.* 266(1):279–286 (Jan. 1991).

Gearing, D.P. et al., "Expression Cloning of a Receptor for Human Granulocyte–Macrophage Colony–Stimulating Factor," *EMBO J.* 8(12):3667–3676 (Dec. 1989).

Gough, N.M. et al., "Localization of the Human GM–CSF Receptor Gene to the X–Y Pseudoautosomal Region," *Nature* 345:734–736 (Jun. 1990).

Lewin, R., "When Does Homology Mean Something Else?" *Science* 237:1570 (Sep. 1987).

Metcalf, D. et al., "Low–Affinity Placenta–Derived Receptors for Human Granulocyte–Macrophage Colony–Stimulating Factor Can Deliver a Proliferative Signal to Murine Hemopoietic Cells" *Proc. Natl. Acad. Sci. USA* 87:4670–4674 (Jun. 1990).

Raines, J.A. et al., "Identification anad Molecular Cloning of a Soluble Human Granulocyte–Macrophage Colony–Stimulating Factor Receptor," *Proc. Natl. Acad. Sci. USA* 88:8203–8207 (Sep. 1991).

Reeck, G.R. et al., "'Homology' in Proteins and Nucleic Acids: A Terminology Muddle and a Way Out Of It," *Cell* 50:667 (Aug. 1987).

*Primary Examiner*—John Ulm
*Attorney, Agent, or Firm*—Sterne, Kessler, Goldstein & Fox PLLC

[57] ABSTRACT

The invention provides a recombinant or synthetic receptor or a derivative thereof, for granulocyte-macrophage colony-stimulating factor (GM-CSF). The GM-CSF receptor is useful, inter alia, in the treatment or diagnosis of GM-CSF-related diseases, and in the screening of agonists and antagonists of GM-CSF receptors. The invention further provides antibodies directed against GM-CSF receptor or derivatives thereof, and pharmaceutical compositions comprising either the GM-CSF receptor, the receptor derivative, or an antibody thereto, and methods of using thereof.

9 Claims, 21 Drawing Sheets

CELL ASSOCIATED RADIOACTIVITY MEASURED
- ▫ IMMEDIATELY AFTER CENTRIFUGATION.
- ▪ AFTER DISSOCIATION FOR 10 MIN. AT 4°C
- ○ BEFORE DISSOCIATION
- ● AFTER DISSOCIATION

CELL ASSOCIATED RADIOACTIVITY MEASURED
- ▫ IMMEDIATELY AFTER CENTRIFUGATION.
- ▪ AFTER DISSOCIATION FOR 10 MIN. AT 4°C
- ○ BEFORE DISSOCIATION
- ● AFTER DISSOCIATION

CELL ASSOCIATED RADIOACTIVITY MEASURED
- ⊡ IMMEDIATELY AFTER CENTRIFUGATION.
- ■ AFTER DISSOCIATION FOR 10 MIN. AT 4°C
- ○ BEFORE DISSOCIATION
- ● AFTER DISSOCIATION

CELL ASSOCIATED RADIOACTIVITY MEASURED
- ⊡ IMMEDIATELY AFTER CENTRIFUGATION.
- ■ AFTER DISSOCIATION FOR 10 MIN. AT 4°C
- ○ BEFORE DISSOCIATION
- ● AFTER DISSOCIATION

```
                    MetProTrpGlyLeuGlnGlnGluAsnProTrpArgGlnGlnIleArgGluAlaAla
AGCAGGTGGAAGGAGAGGAAGCGGATGCCGTGGGGGTTTACAGCAGGAAAATCCGTGGAGACAGCAGATCCGAGAAGCGGC    80

MetPheAla***           MetLeuLeu
GATGTTTGCGTAGAACCCTGTACGTGCTTCCTTCGGCCTGTGCTCTTCCCTTCTCCTTCTCCTTCTGACCAGCACCATGCTTCTCCT    160
                                                                       1
ValThrSerLeuLeuLeuCysGluLeuProHisProAlaPheLeuLeuIleProGluLysSerAspLeuArgThrValAla
GGTGACAAGCCTTCTGCTCTGTGAGTTACCACACCCAGCATTCCTCCTGATCCCAGAGAAATGGATCTGCGAACAGTGG    240
            40                                             ###
ProAlaSerSerLeuAsnValArgPheAspSerArgThrMetAsnLeuSerTrpAspCysGlnGluAsnThrThrPhe
CACCAGCCTCTCAGTCTCAATGTGAGGTTTGACTCCAGGACGATGAATTTAAGCTGGGACTGCCAAGAAAACACAACCTTC    320
       60
SerLysCysPheLeuThrAspLysLysAsnArgValValGluProArgLeuSerAsnAsnGluCysSerCysThrPheArg
AGCAAGTGTTTCTTAACTGACAAGAAGAACAGAGTCGTGGAACCCAGGCTCAGTAACAACGAATGTTCGTGCACATTCG    400
                                                      ###100
GluIleCysLeuHisGluGlyValThrPheGluValHisValAsnThrSerGlnArgGlyPheGlnLysLeuLeuTyr
TGAAATTTGTCTGCATGAAGGAGTCACATTTGAGGTTGAGTGAATACTAGTCAAAGAGAGGATTCAACAGAAACTGCTTT    480
                        120                    ###
ProAsnSerGlyArgGluGlyThrAlaAlaAlaGlnAsnPheSerCysPheIleTyrAsnAlaAspLeuMetAsnCysThr
ATCCAAATTCAGGAAGGAGGGGTACCGCTGCTCAGATTTCTCCTGTTCATCTACAATGCGGATTTAATGAACTGTACC    560
                                   140
TrpAlaArgGlyProThrAlaProArgAspValProArgLeuAspTyrIleArgPheLeuTyrIleArgAsnSerLysArgArgGluIleArg
TGGGCGAGGGGTCCGACGGCCCCCGTGACGTCCAGTATTTTTGTACATACGAAACTCAAAGAGAAGAGGAGATCCG    640
                                                    180   ###
CysProTyrTyrIleGlnAspSerGlyThrHisValGlyCysHisLeuAspAsnLeuSerGlyLeuThrSerArgAsnTyr
GTGTCCTTATTACATACAAGACTCAGGAACCCATGTGGGATGTCACCTGGATAACCTGTCAGGATTAACGTCTCGCAATT    720
```

FIG. 6B

###
PheLeuValAlaAsnGlyThrSerArgGluIleGlnPhePheAspSerLeuLeuAspThrLysLysIleGluArg
ACTTTCTGGTTAACGGAACCAGCCGAGAAATTGGCATCCAATTCTTTGATTCACTTTTGGACACAAAGAAATAGAACGA    800
220                         ###                         240
PheAsnProProSerAsnValThrValArgCysAsnThrThrHisCysLeuValArgTrpLysValArgProArgThrTyrGln
TTCAACCCTCCCAGCAATGTCACGGTACGTTGCAACACGACGCACTGCCTCGTACGGTGGAAACAGCCCAGGACCTATCA    880
                            260
LysLeuSerTyrLeuAspPheGlnLeuGlnTyrArgLysAsnThrGlnProGlyThrGluAsnLeuLeuIle
GAAGCTGTCGTACCTGGACTTTCAGTTGCAGTACCGGAAGAACACCCAGCCTGGCACGGAGAAACCTACTGA    960
280
AsnValSerGlyAspLeuGluAsnArgTyrAsnPheProSerSerProArgAlaLysHisSerValLysIleArg
TAATGTTTCTGGTGATTTGGAAAATAGATACAACTTTCCAAGCTCTCCGAGGGCAAAAACACAGTGAAGATCAGA    1040
300                         ###                         320
AlaAlaAspValArgIleLeuLeuAsnTrpSerSerTrpGluAlaIleGluPheGlySerAspAspGlyAsnLeuGlySer
GCTGCAGACGTCCGCATCTTGCTTAATTGGAGCTCCTGGGAGGCCATTGAATTTGGTTCTGACGACGGGAACCTCGGCTC    1120
                            340
ValTyrIleTyrValLeuLeuIleValGlyIleThrLeuValCysGlyIleIleValLeuGlyPheLeuLysArgPheLeuArg
TGTGTACATTTATGTGCTCCTAATCGTGGGAATCACCCTTGTCTGTGGCATCATCGTCCTCGGCTTCCTCTTTAAAAGGTTCCTTA    1200
                            360
IleGlnArgLeuPheProProValProGlnIleLysAspLysAsnAspAsnHisGluValGluAspIleIle
GGATACAGAGGGCTGTTCCCGCCAGTTCCACAGATCAAAGACAAAACTGAATGATAACCATGAGGTGGAAGACGAGATCATC    1280
380                         400
TrpGluGluPheThrProGluGluGlyLysGlyTyrArgGluGluThrValLysGluIleThr***
TGGGAGGAATTCACCCCAGAGGAAGGGAAAGGCTACCGCGAAGAGGTCTTGACGTGAAGGAAATTACCTGAGACCCAGA    1360
GGGTGTAGGAATGGCATGGACATCTCCGCGACACGGGGAACTGTTTCTTGATGATGCTGTGAACCTTTATAT    1440
CATTTTCTATGTTTTATTTAAAAACATGACATTTGGGGCCAGGCGCGGTGGCTCACGCCTGTAATCCCAGCACTTTGGG    1520

FIG.6C

```
AGGCCAAGGCAGGCGGATCACCTGAGGTCAGGAGTTCAAGACCAGCCTGCCCAACATGGTGAAACCCCATCTGGACTAAA  1600
AATGCAGAAATTTACCCAGGCACGGCGGGGCACGCCCATCATCCCAGCTACTTGGGAGGCTGAGGCAGGAGAATTGCTTG  1680
AACCCGTGAGGCGGAGGTTGTAGTGAGCCAAGATCGCACCATTGCACACCAACCTGCGTGACAGAGCAAGATTGCATCTC  1760
AAAACAAACAATAATAATAAATAAAAACCTGATATTTGGCTGGG(A)n
      ****** ******
```

FIG.6D

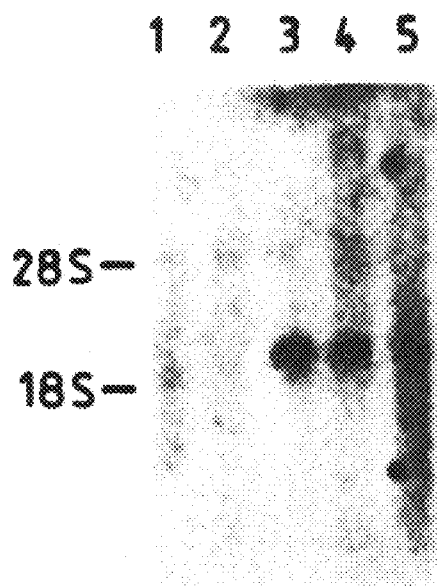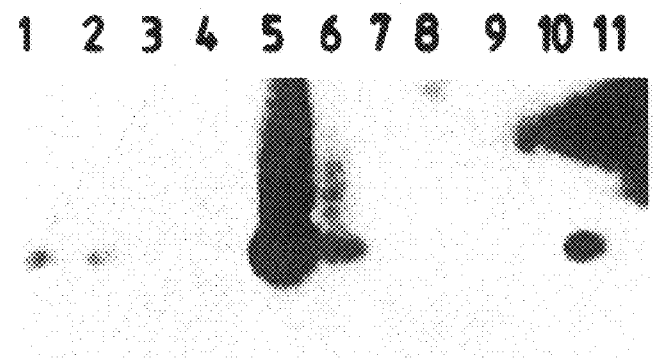
FIG.8A
FIG.8B

|  | (i) | (ii) | (iii) | (iv) | (v) | (vi) | (vii) | *REFERENCE POSITIONS |
|---|---|---|---|---|---|---|---|---|
|  | (*) | (*) | (*) | (*) | (*) | (*) | (*) |  |
| hGMR | ..SCF | ....CTW | ....C | ....CHL | ....RW | ....VKIRAA—DVRILN—WSSWS | ...LIVGTLVC-GIVLGF |  |
| hIL6R | ..SCF | ....CEW | ....C | ....CQL | ....RW | ....VQLRAQ—EEFGQGEWSEWS | ...LAFGTLLCIAIVLRF |  |
| mEPOR | ..LCF | ....CFW | ....C | ....CSL | ....RW | ....VRARMA—EPSFSGFWSAWS |  |  |
| hIL2Rb | ..TCF | ....CVW | ....C | ....CVW | ....SW | ....VRVKPLQGEFTT——WSPWS |  |  |
| Cons. | ..CF | ....C.W | ....C | ....C.1 | ....rW | ....V.R..E.....WS.WS | ...L..GTL.C..IVL.F |  |
|  |  |  |  |  |  |  K  D |  |  |
| rPRLR | ..KCR | ....CWW | ....C | ....CFF | ....KW | ....VQTRCKP-DHGY——WSRWS |  |  |

FIG.9B

ANTIBODIES WHICH BIND GRANULOCYTE-MACROPHANE COLONY-STIMULATING FACTOR RECEPTOR

CROSS-REFERENCE TO RELATED APPLICATIONS

This application is a continuation of U.S. application Ser. No. 08/384,828, filed Feb. 7, 1995, now U.S. Pat. No. 5,726,036, which is a division of U.S. application Ser. No. 08/351,149, filed Nov. 23, 1994, now U.S. Pat. No. 5,629,283, which is a continuation of U.S. application Ser. No. 07/834,534, filed Apr. 10, 1992, now abandoned, which is a 35 U.S.C. §317 application claiming the benefit of PCT/AU90/00342, filed Aug. 10, 1990. The contents of U.S. application Ser. No. 08/384,828, filed Feb. 7, 1995, now U.S. Pat. No. 5,726,036, and U.S. application Ser. No. 08/351,149, filed Nov. 23, 1994, now U.S. Pat. No. 5,629,283, are entirely incorporated herein by reference.

BACKGROUND OF THE INVENTION

1. Field of the Invention

The present invention relates generally to human recombinant and synthetic granulocyte-macrophage colony stimulating factor (GM-CSF) low-affinity receptor proteins, antibodies and to derivatives thereof. These proteins are useful inter alia in the preparation of therapeutics and diagnostics and in the generation of agonist and antagonist compounds with respect to the binding GM-CSF to its receptor, which are also part of the present invention, including diagnostic and pharmaceutic compositions thereof. The present invention also provides diagnostic and therapeutic methods using the above proteins and compositions.

2. Related Art

Granulocyte-macrophage colony-stimulating factor (GM-CSF) is a glycoprotein growth and differentiation factor which regulates the proliferation, differentiation and functional activity of cells of the neutrophil, eosinophil and monocyte/macrophage series (reviewed in Metcalf, D., *The Hemopoietic Colony Stimulating Factors*, Elsevier, Amsterdam (I1984) and Gough, N. M. and Nicola, N. A., in *Colony-Stimulating Factors: Molecular and Cellular Biology*, Hexter, T. M. et al., eds., Marcel Dekker, New York, pp. 111–153 (1989). Molecular clones encoding murine (Gough, N. M. et al., *Nature* 309:763–767 (1984)) and human (Wong, G. G. et al., *Science* 228:810 (1985)) GM-CSF have been isolated, and recombinant protein tested in animal model systems (Metcalf, D. et al., *Exp. Hematol.* 15:1–9 (1987), Donohue, R. E. et al., *Nature* 321:827–875 (1986)) and in phase I/II clinical trials in patients with a variety of hemopoietic disorders (reviewed in Morstyn, G. et al., *Trends Pharmacol. Sci.* 10:154–159 (1989)). In both animal experiments and clinical trials, GM-CSF has been found to elevate circulating levels of monocytes, neutrophils and eosinophils; to enhance the functional capacities of the circulating cells; and to enhance the rate of hemopoietic recovery following chemotherapy and/or bone marrow transplantation (Gough, N. M. and Nicola, N. A., in *Colony-Stimulating Factors: Molecular and Cellular Biology*, Hexter, T. M. et al., eds., Marcel Dekker, New York, pp. 111–153 (1989); Morstyn, G. et al., *Trends Pharmacol. Sci.* 10:154–159 (1989)).

In both murine and human systems, autoradiographic analyses have indicated that GM-CSF receptors are present in low numbers (a few hundred per cell) on cells within the monocyte, neutrophil and eosinophil lineages (Nicola, N. A., *Immunol. Today* 8:134–139 (1987); DiPersio, J. et al., *J. Biol. Chem.* 263:1834–1840 (1988)). However, functional GM-CSF receptors have also been detected on non-hemopoietic cells, including endothelial cells (Bussolino, F. et al, *Nature* 337:471–473 (1989)), small-cell lung carcinoma cell lines and SV40-transformed simian COS cells (Cocita Baldwin, G. et al., *Blood* 73:1033–1037 (1989)).

In the murine system, Walker, F. and Burgess, A. W., *EMBO J* 4:933–939 (1985) detected both high-affinity ($K_D$ about 30 pM) and low-affinity ($K_D$ about 1 nM) receptors, while Park, L. L. et al., *J. Biol. Chem.* 261:4177–4183 (1986) detected a single receptor class of $K_D$ 1–3 nM. In the human system, only high-affinity receptors have been described on hemopoietic and endothelial cells ($K_D$ about 30 pM) (Gasson, J. C. et al., *Proc. Natl. Acad. Sci. (USA)* 83:669–673 (1986); Bussolino, F. et al., *Nature* 337:471–473 (1989); Park, L. L. et al., *J. Exp. Med.* 164:251–262 (1986)), but a receptor of lower affinity has been described on COS cells (Cocita Baldwin, G. et al., *Blood* 73:1033–1037 (1989)). In the murine system, the GM-CSF receptors recognize only GM-CSF, although they can be indirectly down-modulated by interleukin-3 and other agents (Walker, F. et al., *Cell* 45:269–276 (1985); Nicola, N. A., *Immunol. Today* 8:134–139 (1987)).

Because most of the biological effects of GM-CSF are observed at picomolar concentrations (Metcalf, D., *The Hemopoietic Colony Stimulating Factors*, Elsevier, Amsterdam (1984)), and because we have found that high-affinity receptors are preferentially internalized (Gough, N. M. and Nicola, N. A., in *Colony-Stimulating Factors: Molecular and Cellular Biology*, Hexter, T. M. et al., eds., Marcel Dekker, New York, pp. 111–153 (1989)), it is not clear whether low-affinity receptors are biologically functional in the murine system at 37° C. (Walker, F. et al., *Cell* 45:269–276 (1985)) and in the human system at 4° C. or 37° C. (Elliot, M. J. et al., *Blood* 74:2349–2359 (1989); Lopez, A. F. et al., *Proc. Natl. Acad. Sci. (USA)* 86:7022–7026 (1989); Park, L. S. et al., *J. Biol. Chem.* 264:5420–5427 (1989)), Multi-CSF (interleukin-3) can down-modulate GM-CSF receptors on some types of hemopoietic cells, but it is not clear whether this is mediated by different receptor subclasses or by receptor-receptor interactions (Gearing et al., 1989; Elliot, M. J. et al., *Blood* 74:2349–2359 (1989); Lopez, A. F. et al., *Proc. Natl. Acad. Sci. (USA)* 86:7022–7026 (1989)).

GM-CSF was originally defined by its ability to stimulate the proliferation of granulocyte/macrophage progenitor cells, but more recently it has become apparent that it can also stimulate the proliferation of progenitor cells of other hemopoietic lineages (Metcalf, D. et al., *Blood* 55:138–147 (1980)) and cells of non-hemopoietic origin. The latter include human bone marrow fibroblasts, osteogenic sarcoma cell lines and a breast carcinoma cell line (Dedhar, S. et al., *Proc. Natl. Acad. Sci. (USA)* 85:9253–9257 (1988)), human small cell carcinoma cell lines (Cocita Baldwin, G. et al., *Blood* 73:1033–1037 (1989)), human endothelial cells (Bussolino, F. et al., *Nature* 337:471–473 (1989)) and human placental cells (Wegmann, T. G. et al., *Transplant. Proc.* 21:566–568 (1989)). In addition, GM-CSF stimulates human endothelial cell migration (Bussolino, F. et al., *Nature* 337:471–473 (1989)), the proliferation and function of human osteoblast-like cells in vitro (Evans, D. B. et al., *Biochem. Biophys. Res. Commun.* 160:588–595 (1989)) and improves the growth of murine placental cells in vivo (Wegmann, T. G. etal., *Transplant. Proc.* 21:566–568 (1989)).

In view of these biological results, it is apparent that the GM-CSF receptors detected on these cells are functional, despite the fact that only high affinity receptors were detected on the endothelial cells, whereas only low affinity receptors were detected on- the fibroblasts and placental membranes.

On hemopoietic cells, low affinity hGM-CSF receptors were distinguished by a rapid rate of ligand dissociation and poor internalization at 37° C., whereas high affinity receptors displayed a much slower rate of ligand dissociation, and were efficiently internalized. In addition to this complexity, two types of high affinity hGM-CSF receptor have been described on some but not all normal hemopoietic cells and cell lines. One type recognizes only hGM-CSF and is the only type of GM-CSF receptor on human neutrophils, while the other type apparently recognizes hGM-C-SF and h-IL-3 with nearly equal affinity, and represents 80% of GM-CSF receptors on eosinophils (Lopez, A. F. et al., *Proc. Natl. Acad. Sci.* (*USA*) 86:7022–7026 (1989)). Reciprocally, IL-3-specific or cross-reactive receptors have also been described (Park, L. S. et al., *J. Biol. Chem.* 264:5420–5427 (1989)).

Finally, cross-linking experiments have suggested a molecular weight for the murine GM-CSF receptor of 51,000 (Walker, F. and Burgess, A. W., *EMBO J.* 4:933–939 (1985)) or 130,000 (Park, L. L. et al., *J. Biol. Chem.* 261:4177–4183 (1986)), while the human receptor molecular weight has been estimated at 84,000 (DiPersio, J. et al., *J. Biol. Chem.* 263:1834–1840 (1988)).

Although some of the properties of GM-CSF receptor have been deduced, the receptor has not hitherto been isolated or purified.

SUMMARY OF THE INVENTION

In accordance with the present invention, there is provided a gene encoding the human GM-CSF receptor. The expression of this gene provides an isolated quantity of recombinant receptor heretofore unavailable, thereby permitting, inter alia, the development of receptor polypeptides, derivatives, antibodies, therapeutics, diagnostics, agonists and antagonists, and the like.

Accordingly, a first aspect of the present invention relates to human recombinant or synthetic GM-CSF receptor and its derivatives, e.g., comprising that portion of the receptor comprising its soluble (non-membrane associated) region that has the capacity to bind GM-CSF.

A second aspect of the present invention relates to antibodies that recognize human recombinant or synthetic GM-CSF receptor (and its derivatives), and which are useful in the detection and/or purification of these molecules.

A third aspect of the present invention relates to modulating the binding of GM-CSF to its cell-bound receptor with agonists or antagonists of GM-CSF.

A fourth aspect of the present invention contemplates a method of treatment of GM-CSF related diseases in a mammal, and in particular a human, by the administration to said mammal of an effective amount of recombinant or synthetic GM-CSF receptor or its derivative. One such method involves modulating the proliferation, differentiation or functional activation of GM-CSF-stimulation-sensitive cells in the mammal, which method comprises the administration to said mammal of an effective amount of recombinant or synthetic GM-CSF receptor or its derivative for a time and under conditions sufficient to reduce the amount of non-bound GM-CSF in said mammal. An effective amount can readily be determined by routine experimentation, as can the most effective and/or convenient route of administration, such as parenteral (e.g., intravenous, intramuscular, subcutaneous, and the like) or oral. Slow release formulations may be advantageous for specific purposes. Preferably the mammal and the origin of the GM-CSF receptor are homologous, and even more preferably the homologous system is human.

A fifth aspect of the present invention, provides a method for diagnosing cancers and/or other GM-CSF related diseases composed of, or associated with, GM-CSF-stimulation sensitive cells in a mammal, the method comprising the detection of GM-CSF receptor or aberrations thereof. In this aspect, the invention also extends to kits for such diagnostic purposes. For example, diagnostic kits for assays utilizing radioimmunoassays, fluorescent immunoassay, or ELISA are examples of those included in the invention.

A sixth aspect of the present invention relates to the use of recombinant or synthetic human GM-CSF receptor in the manufacture of a medicament for the treatment of GM-CSF related diseases.

A seventh aspect of the invention relates to a GM-CSF-dependent hemopoietic cell line into which a low affinity receptor for a heterologous GM-CSF has been cloned.

An eighth aspect of the invention relates to a method of screening a cDNA library for a cDNA fragment encoding GM-CSF receptor, comprising the steps of:

constructing a cDNA library, preparing cDNA fragments therefrom, transfecting said fragments into mammalian host cells, incubating said transfected cells with labelled GM-CSF, identifying populations of transfected cells binding said labelled GM-CSF, preparing clones of host cells transformed with cDNA fragments able to cause mammalian host cells to bind labelled GM-CSF, and isolating said clones.

BRIEF DESCRIPTION OF THE FIGURES

The present invention is further described by way of reference to the following figures, in which:

In FIGS. 1A, 1C, $5\times10^6$ DMSO-treated HL60 cells per point were incubated with increasing concentrations of $^{125}$I-hGM-CSF at 4° C. for 3 hours and specific cell-associated radioactivity measured immediately after centrifugation or after 10 minute incubation in 1 ml phosphate buffered saline (PBS) at 4° C. Scatchard analyses of these binding data are shown in FIG. 1C before or after dissociation. The computer-derived high- and low-affinity binding components for undissociated cells are shown as solid lines.

In FIGS. 1B, 1D, 40 $\mu$l of human placental membrane suspension, prepared as in Example 1, were incubated with increasing concentrations of $^{125}$I-hGM-CSF at 20° C. for 1 hour and specific binding subjected to Scatchard transformation, as is shown in FIG. 1D.

with or without the same amounts of unlabelled hGM-CSF or hIL-3 as above. Total binding to each membrane preparation (mean±range) is shown.

FIGS. 3A–E show the detection and specificity of hGM-CSF receptors transfected to COS-7 cells.

Figure 3A:
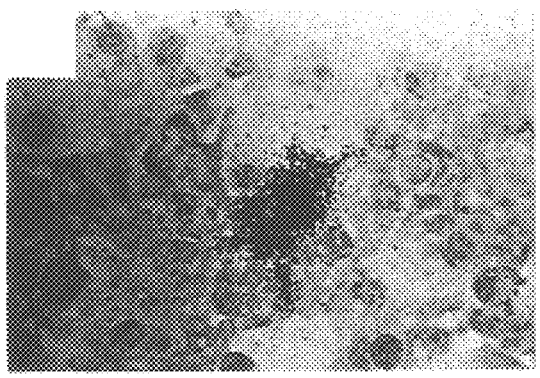

FIG. 3A is a photomicrograph of the cell autoradiograph showing the single clearly positive cell detected in $1.5 \times 10^6$ COS-7 cells transfected with Pool 138 of the cDNA library (the COS cell covered by autoradiographic grains); magnification ×20.

Figure 3B:
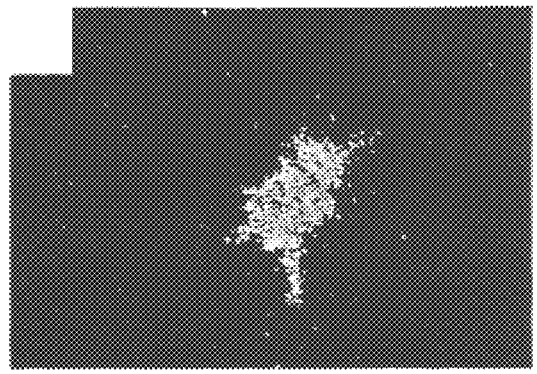

FIG. 3B is the same as FIG. 3A, but photographed under dark field illumination.

Figure 3C:
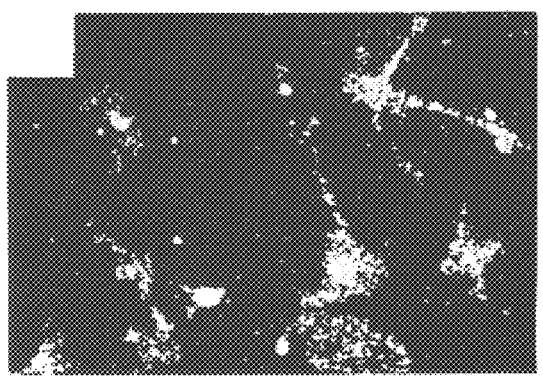

FIG. 3C shows dark field illumination of a cell autoradiograph of COS-7 cells transfected with a pure hGM-CSF receptor clone (clone pGMR138) and incubated with 2 nM $^{125}$I-hGM-CSF; magnification ×10.

Figure 3D:
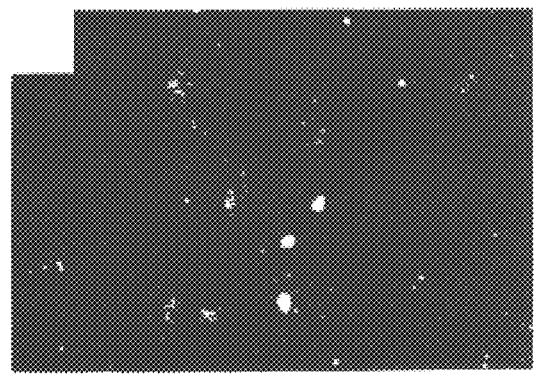

FIG. 3D is the same as FIG. 3C, except that cells were also incubated with 20 nM unlabelled hGM-CSF. Note dramatic reduction in autoradiographic grains.

Figure 3E:
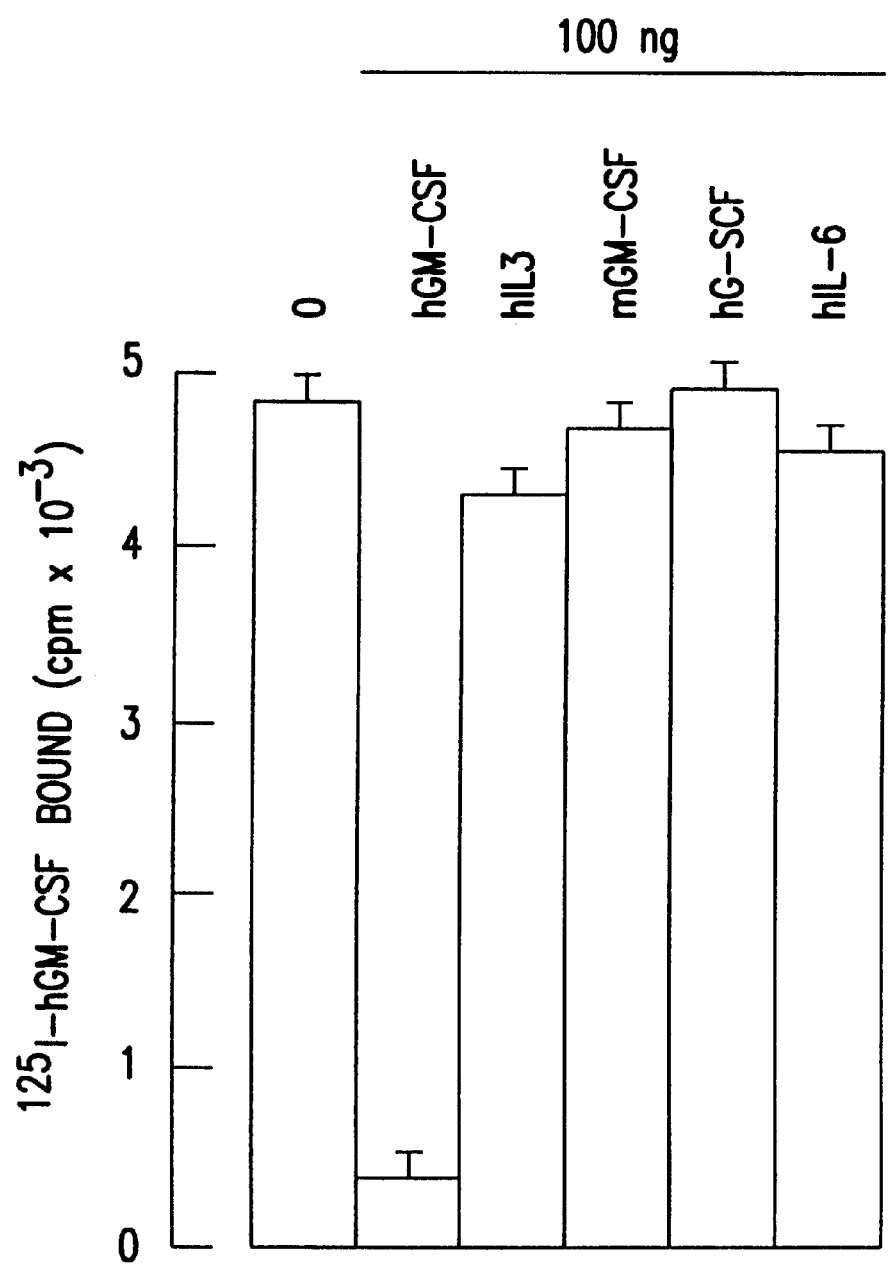

FIG. 3E shows the specificity of the placental hGM-CSF receptor transfected to COS-7 cells. COS-7 cells transfected 48 hours earlier with the pure clone (pGMR138) were assayed in duplicate for their ability to bind $^{125}$I-hGM-CSF in the absence or presence of 100 ng unlabelled hGM-CSF, h-IL-3, murine GM-CSF, human G-CSF or human IL-6 (mean±range). Transfected cells (30,000 per point) were incubated for 1 hour at 20° C. in HRF containing 20 mM EDTA and 100 pg/ml chondroitin sulphate and $^{125}$I-hGM-CSF (70,000 cpm in 100 µl).

Figure 4A:
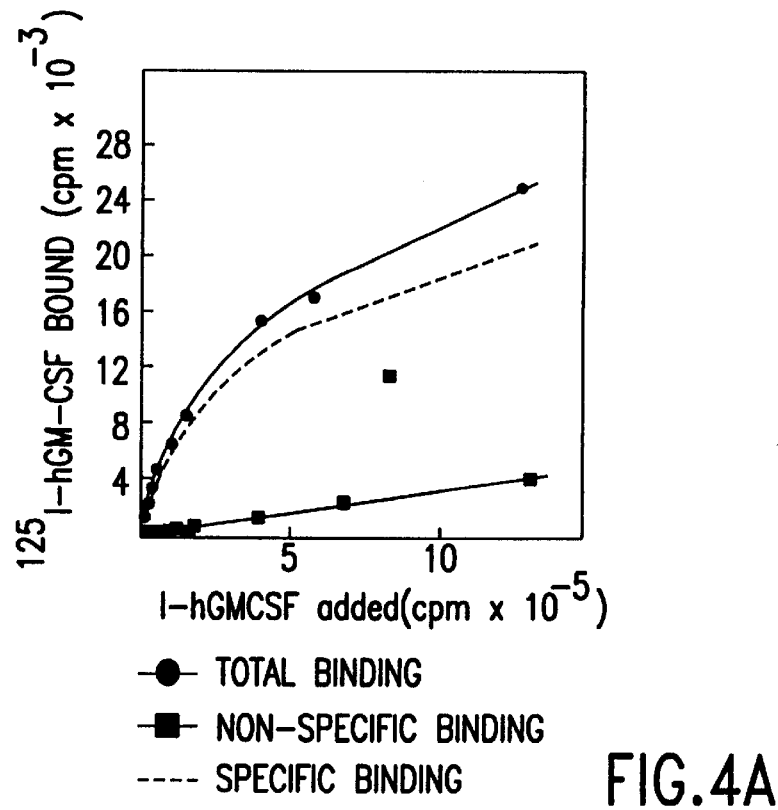
Figure 4B:
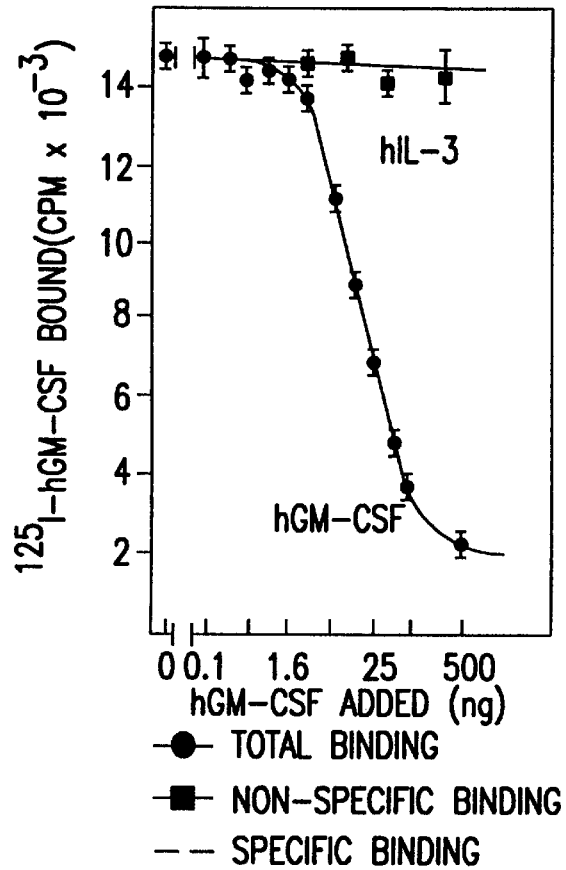
Figure 4C:
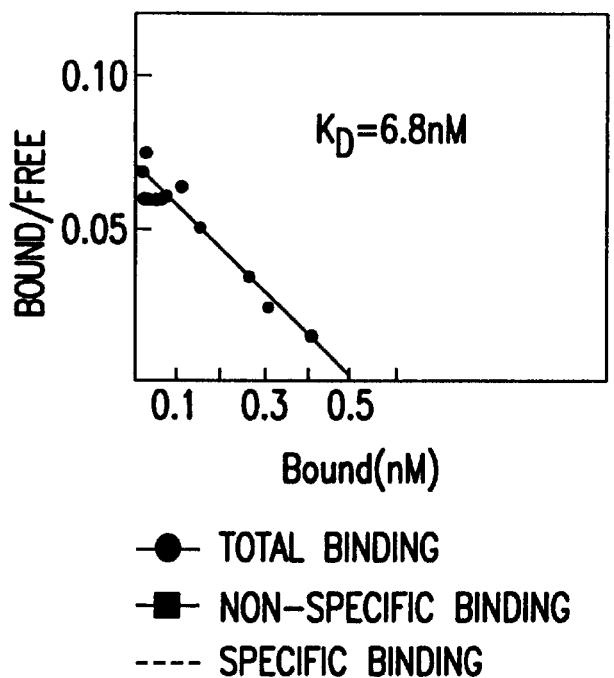

FIGS. 4A–D show saturation and competition binding analysis of the placental hGM-CSF receptor transfected to COS-7 cells. COS-7 cells (33,000 per point) transfected 48 hours earlier with the pure clone (pGMR138) were incubated with increasing concentrations of $^{125}$I-hGM-CSF (200,000 cpm) (FIGS. 4A, 4C) or a constant amount of $^{125}$I-hGM-CSF and increasing concentrations of unlabelled hGM-CSF or h-IL-3 (FIGS. 4B, 4D) in a constant volume of 85 µl HRF/20 mM EDTA/100 µg/ml chondroitin sulphate at 20° C. for 1.5 hours. In FIG. 4A, total binding, non-specific-binding and specific binding are shown with Scatchard transformation of the specific binding data shown in FIG. 4C. In FIG. 4B, total binding is shown in the upper panel, with Scatchard transformation of the specific binding data shown in FIG. 4D.

Figure 5:
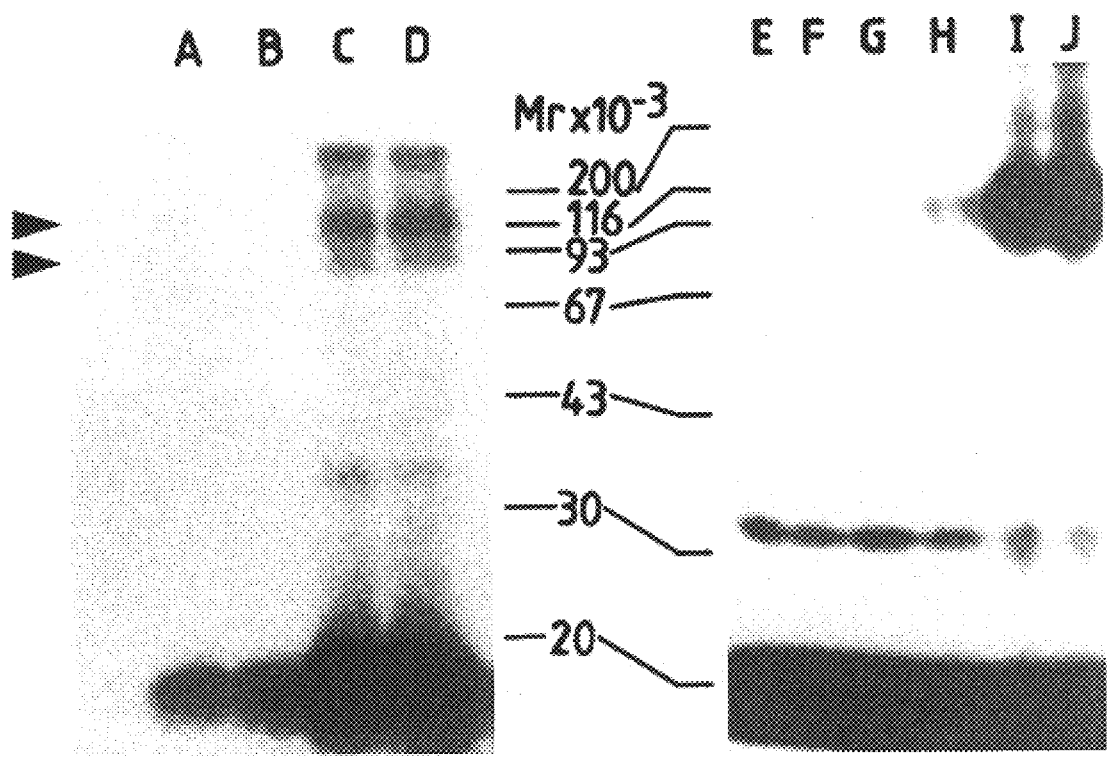

FIG. 5 shows an analysis of chemical cross-linking of the hGM-CSF receptor on DMSO-treated HL60 cells and on transfected COS-7 cells, using SDS-polyacrylamide gel electrophoresis. In tracks A–D, $5 \times 10^6$ HL60 cells treated for 9 days with DMSO were used per point while in tracks E–J, $7 \times 10^4$ transfected COS-7 cells were used per point. In each case binding was for 3 hours at 4° C. with $^{125}$I-hGM-CSF at 2 nM. Tracks C and D were with or without 10 minute dissociation in 1 ml PBS to remove low-affinity binding, and A and B are as for C and D except that 20 nM unlabeled hGM-CSF was included during the binding reaction. In each case 1 mM DSS was used for cross-linking (15 minutes on ice). Tracks E–J represent transfected COS cells allowed to bind $^{125}$I-hGM-CSF and then cross-linked with E, 0 mM; F, 0.01 mM; G, 0.05 mM; H, 0.1 mM; I, 0.5 mM and J, 1 mM DSS for 15 minutes on ice. Gel electrophoresis was on 10% (w/v) SDS gels (A–D) or 8% (w/v) SDS gels (E–J) and autoradiographs were exposed for 4 weeks (A–D) or 2 days (E–J). Molecular weight markers (Pharmacia and BioRad) are shown.

Figure 6A:
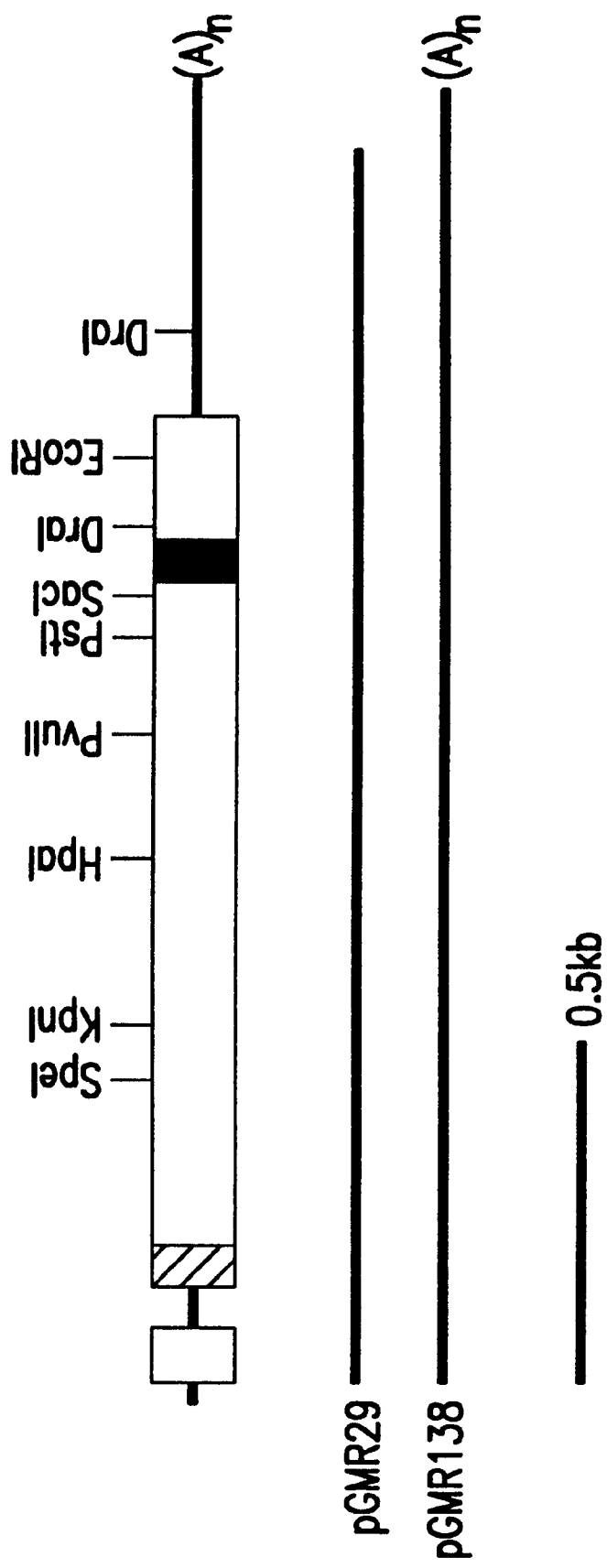

FIGS. 6A–D show a restriction map and the nucleotide and amino acid sequences (SEQ ID NOS:4 and 6) of the insert cDNAs of plasmids pGMR138 and pGMR29. FIG. 6A represents a restriction endonuclease cleavage map of the insert cDNAs of pGMR138 and pGMR29. Boxes represent open reading frames. The hatched and filled regions represent the signal sequence and transmembrane region of the GM-CSF-R coding region, respectively. The stippled box represents the upstream open reading frame. FIGS. 6B–D show the combined nucleotide sequence and deduced amino acid sequence of the insert cDNAs of pGMR138 and pGMR29. Numbers at the right margin indicate positions of nucleotides and numbers above the sequence refer to the amino acid sequence. The hatch marks indicate potential N-glycosylation sites (Asn-X-Ser/Thr). The overlined regions indicate the presumed signal peptide and transmembrane region, respectively. The sets of six asterisks identify possible poly(A) addition signals. The poly(A) tail in clone 138 was 61 nucleotides long. Fragments of the GM-CSF receptor protein include 1-22, 2-22, 23-319, 294-310, 320-346, 347-400 and 331-344 of SEQ ID NO:6.

Figure 7:
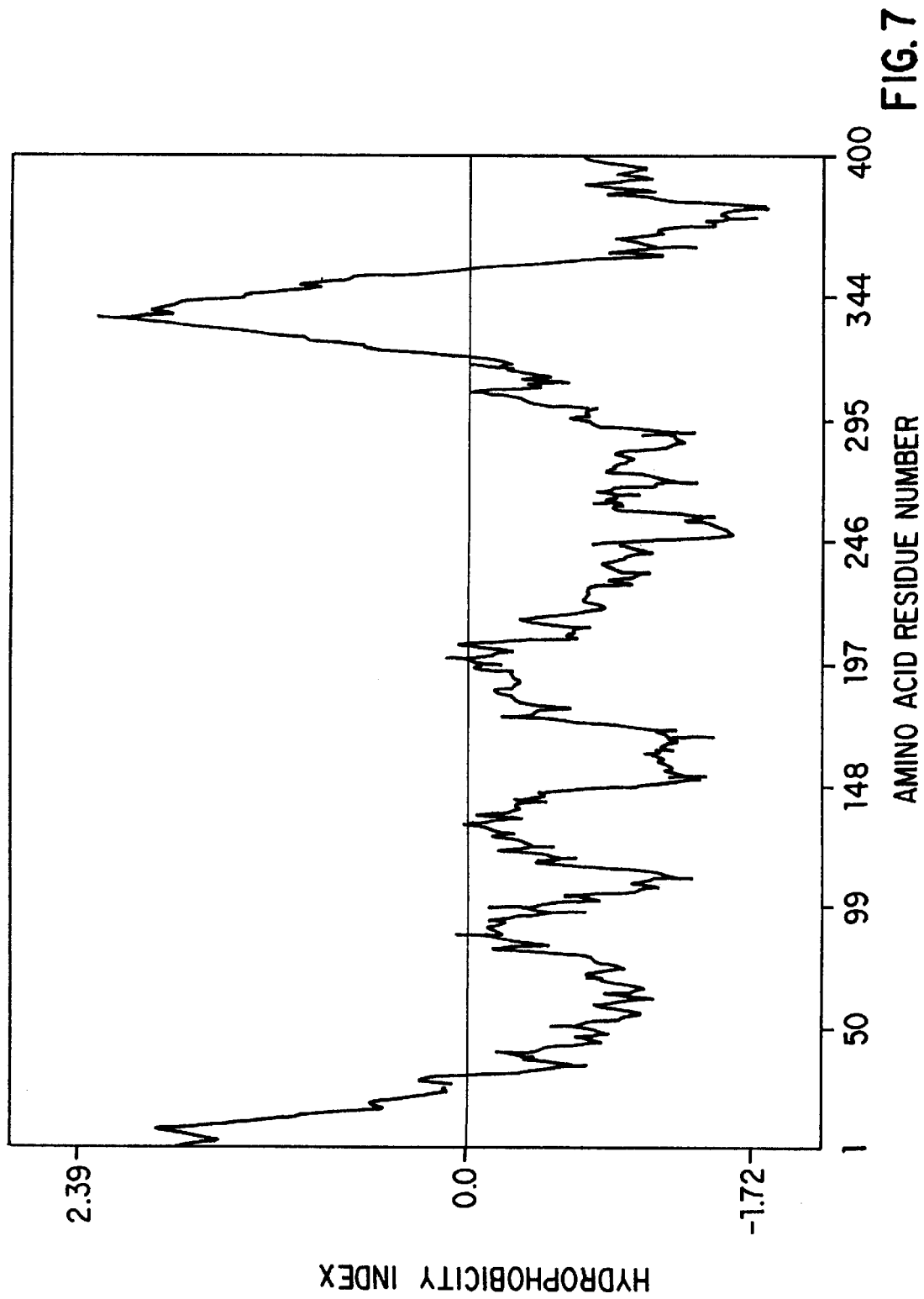

FIG. 7 is a hydrophobicity plot of the hGM-CSF receptor sequence obtained using a method as described in Hopp, T. P. and Woods, K. R., *Mol. Immunol.* 20:483–489 (1983) (span length=15). Note the two hydrophobic regions corresponding to the signal sequence and transmembrane domain, respectively.

FIGS. 8A–B are a photograph showing the detection of the human GM-CSF receptor transcript.

In FIG. 8A, RNA from the following sources was probed for hGM-CSF receptor transcripts by Northern blot analysis as described in Example 1: CEM cells (Track 1); HepG2 cells (Track 2); HL60 cells (Tracks 3 and 4); HL60 cells cultured at $5 \times 10^5$ cells/ml with 100 ng/ml TPA for 3 days (Track 5). The positions of the 28S and 18S rRNA molecules are indicated. On other gels, RNA size standards (BRL) were also included. Exposure time of the autoradiograph: 5 days.

In FIG. 8B, RNA from the following sources was probed for hGM-CSF receptor transcripts by PCR-based amplification of cDNA as described in Example 1: U937 cells (Track 1); AML193 cells (Track 2); HL60 cells (Tracks 5 and 6); CEM cells (Track 7); Raji cells (Track 8); Hep G2 cells (Track 9); HeLa cells (Track 10). Tracks 3, 4 and 11 contained the following negative controls: "RNA blank" from no cells, carried through cDNA synthesis and PCR reactions; HL60 RNA not subjected to cDNA synthesis; and murine 160T cells, respectively.

Figure 9A:
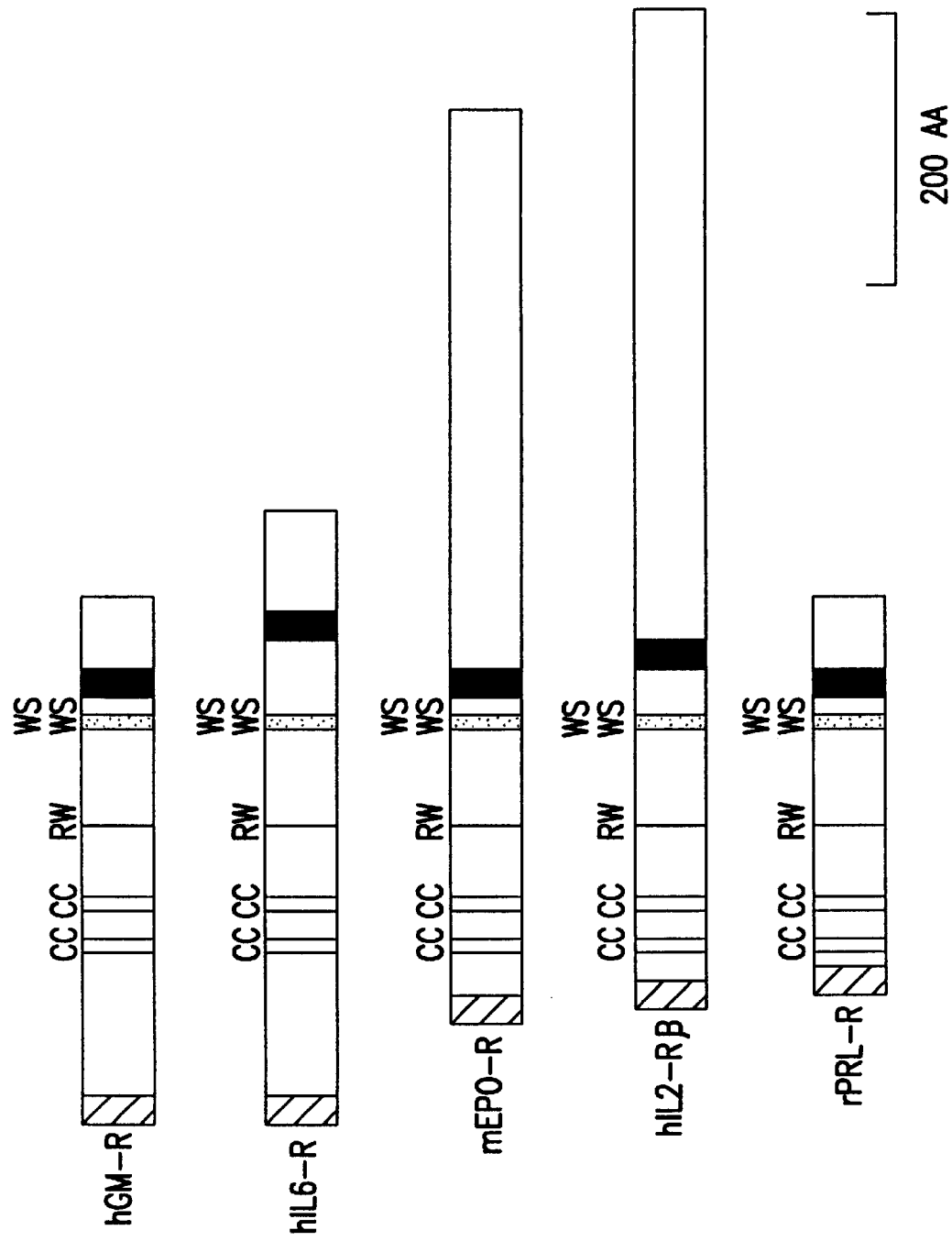

FIGS. 9A–B depict the alignment of the sequence of the hGM-CSF-receptor with other growth factor receptors. Amino acids are identified using the single letter abbreviations standard in the art.

FIG. 9A shows a schematic of alignment: Boxes represent coding regions. The hatched and solid boxes represent signal sequences and transmembrane regions, respectively. The positions of four conserved cysteine residues (L) and a conserved tryptophan residue (W) are indicated by vertical lines. The stippled box represents the "WS—WS" box. Sequences are aligned via the first conserved cysteine residue.

FIG. 9B shows the details of Sequence Alignment: Reference positions (*) are marked above the-sequence (i–vii) and correspond to the following amino acid numbers of each sequence (numbers in brackets refer to positions (i)–(vii), respectively): hGMR (SEQ ID NO:8) (126, 136, 165, 178, 236, 294, 331), hIL6R (SEQ ID NO:9) (121, 132, 165, 176, 233, 290, 374), mEPOR (SEQ ID NO:10) (52, 62, 90, 106, 165, 219, NH), hIL2R (SEQ ID NO:11) (36, 46, 60, 74, 126, 182, NH) and rPRLR (SEQ ID NO:13) (31, 41, 70, 81, 146, 199, NH). The fragments shown for hGMR include residues 294-310 and 332-344 of SEQ ID NO:6. NH: no homology; Cons (SEQ ID NO:12): consensus sequence based on hemopoietic receptor sequences. Except in the consensus, dots indicate variable spacing and dashes indicate gaps introduced to align the sequences.

Figures 10A, 10B:
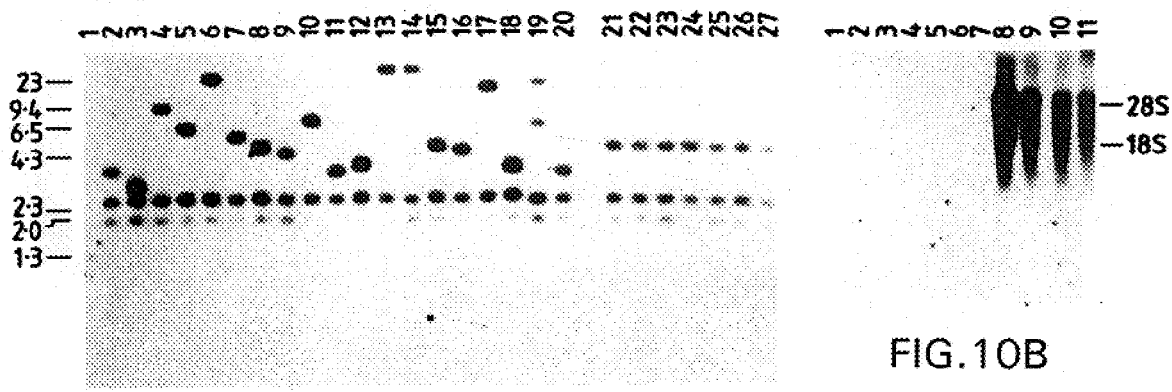

FIGS. 10A–B show viral integration and transcripts in hGM-R-FD cells.

In FIG. 10A, DNA from FDC-P1 cells (track 1), hGM-R-FD clones 1, 6, 8, 10, 11, 13, 21, 24, 33, 34, 49, 50, 52, 53, 54, 55, 56, 57 and 58 (tracks 2–20) and hGM-R-FD clones 21, 21.13, 21.15, 21.17, 21.21, 21.22 and 21.23 (tracks 21–27) was digested with Pst I and probed for hGM-R sequences as described in Example 1. Note the common 2.5 Kbp fragment derived from within the hGM-R viral construct.

In FIG. 10B, total cytoplasmic RNA from FDC-P1 cells (track 1) and hGM-R-FD clones 21.13, 21.15, 21-17, 21-21, 21.22, 21.23, 21.7, 21.8, 21.10 and 21.11 (tracks 2–11) was probed for viral hGM-R transcripts as described in Example 1. The major species is 5.5 Kb in length and corresponds to the full-length unspliced viral transcript.

Figure 11A:
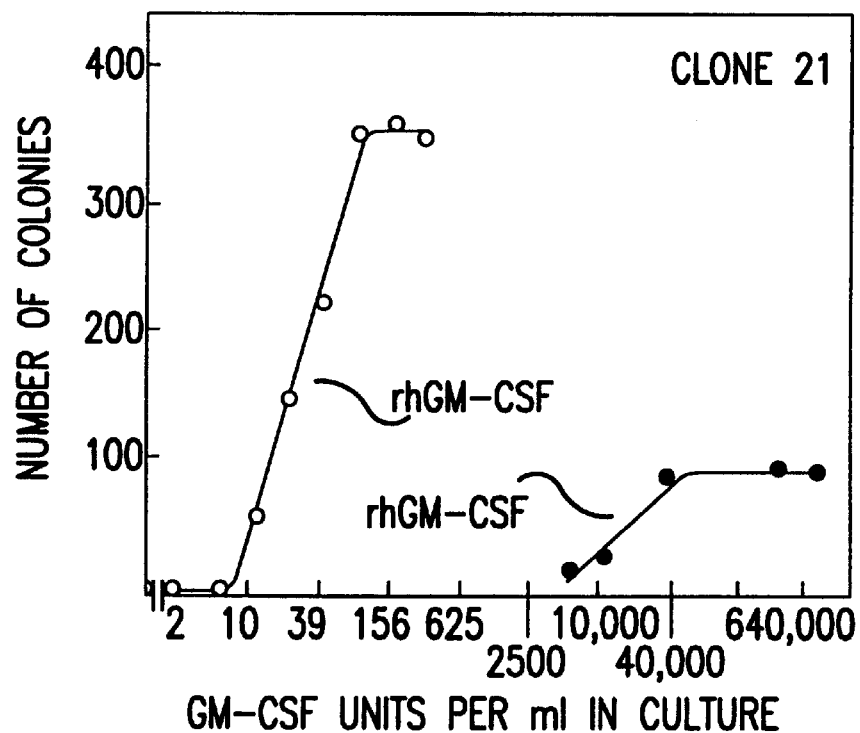
Figure 11B:
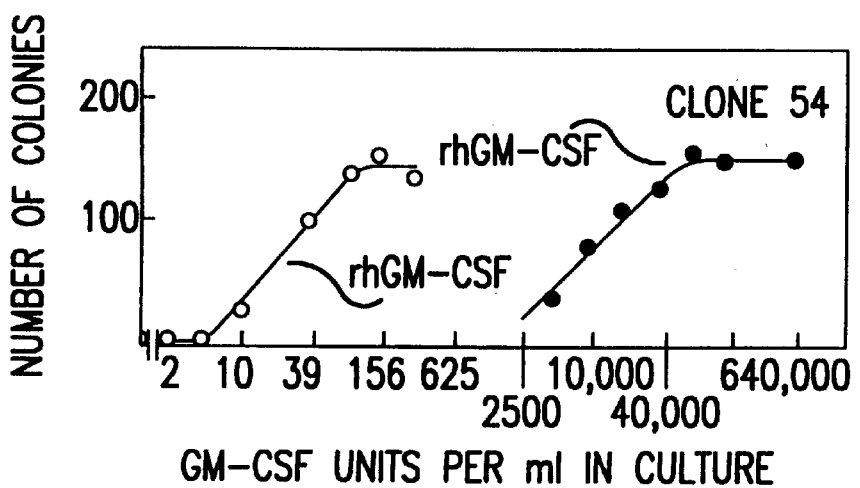
Figure 12A:
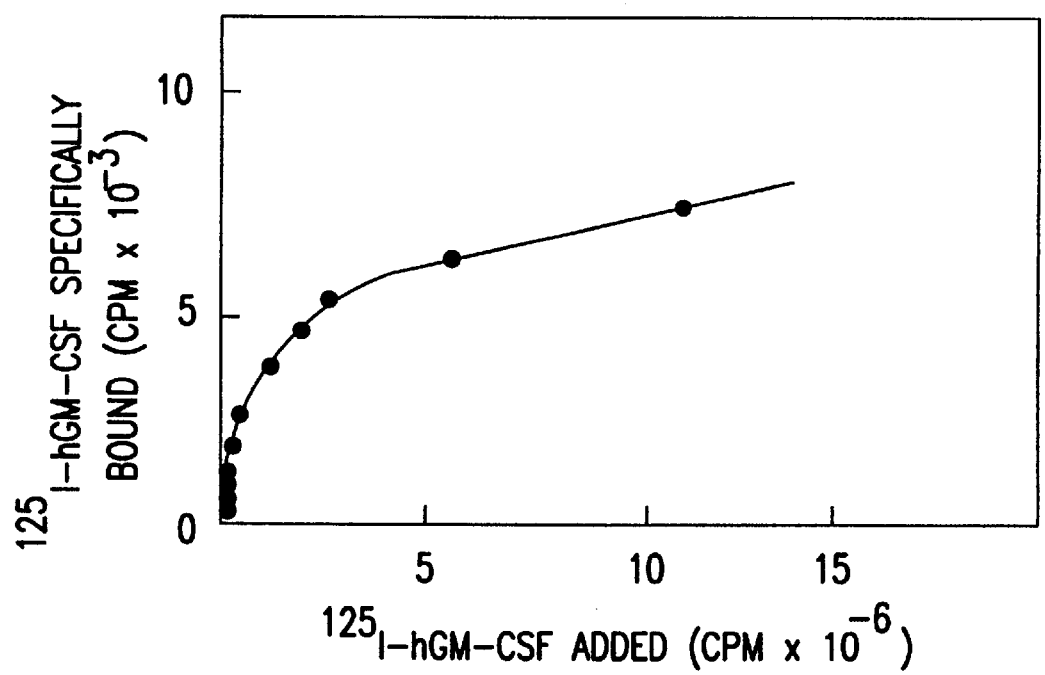
Figure 12B:
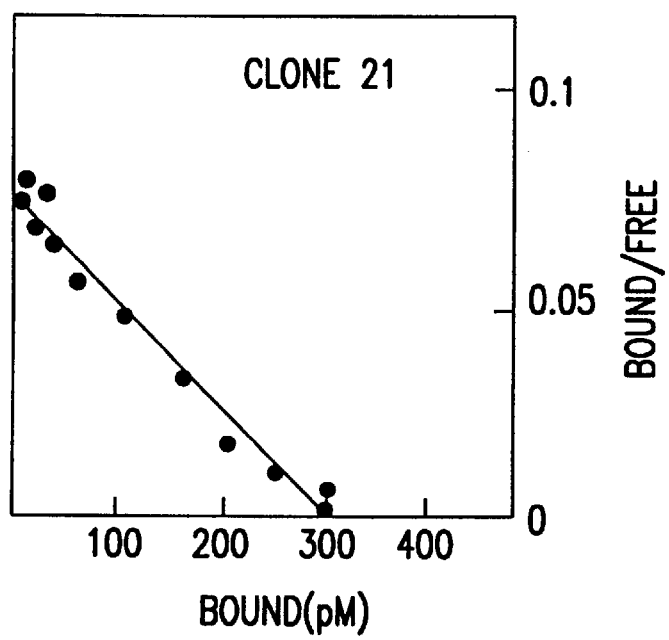
Figure 12C:
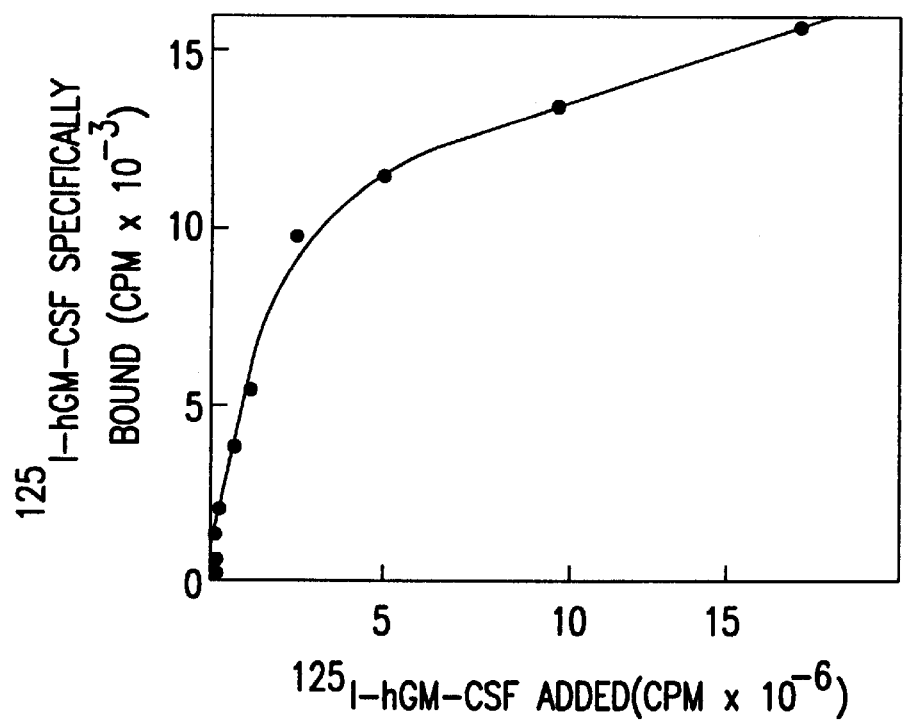
Figure 12D:
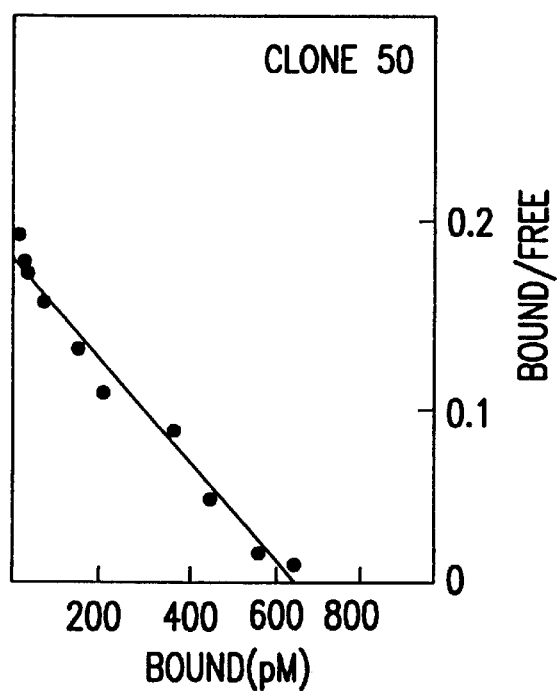

FIGS. 11A–B illustrate the responsiveness of cells from cloned hGMR-FD cell lines to proliferative stimulation by recombinant m- or hGM-CSF. Lines maintained in human GM-CSF exhibit a similar content of clonogenic cells with both stimuli (e.g., clone 54, FIG. 11B ), whereas in lines maintained in m+hGM-CSF (e.g., clone 21, 11A) murine-responsive clonogenic cells are more frequent than human-responsive cells. For both types of cell lines, clonogenic cells are less responsive to human than to murine GM-CSF.

FIGS. 12A–D show saturation binding analysis and Scatchard transformation of $^{125}$I-hGM-CSF binding to hGM-R-FD cell clones. 12A, 12B: clone 21 maintained in h+mGM-CSF, $2\times10^6$ cells per point; 12C, 12D: clone 50 maintained in hGM-CSF only; $0.8\times10^6$ cells per point. 12A and 12C are specific binding curves with increasing amounts of $^{125}$I-hGM-CSF added and 12B and 12D are the Scatchard transformations. The Scatchard transformations gave $K_D=4$ nM and 4,000 receptors/cell for clone 21 and $K_D=6$ nM and 20,000 receptors/cell for clone 50.

Figure 13A:
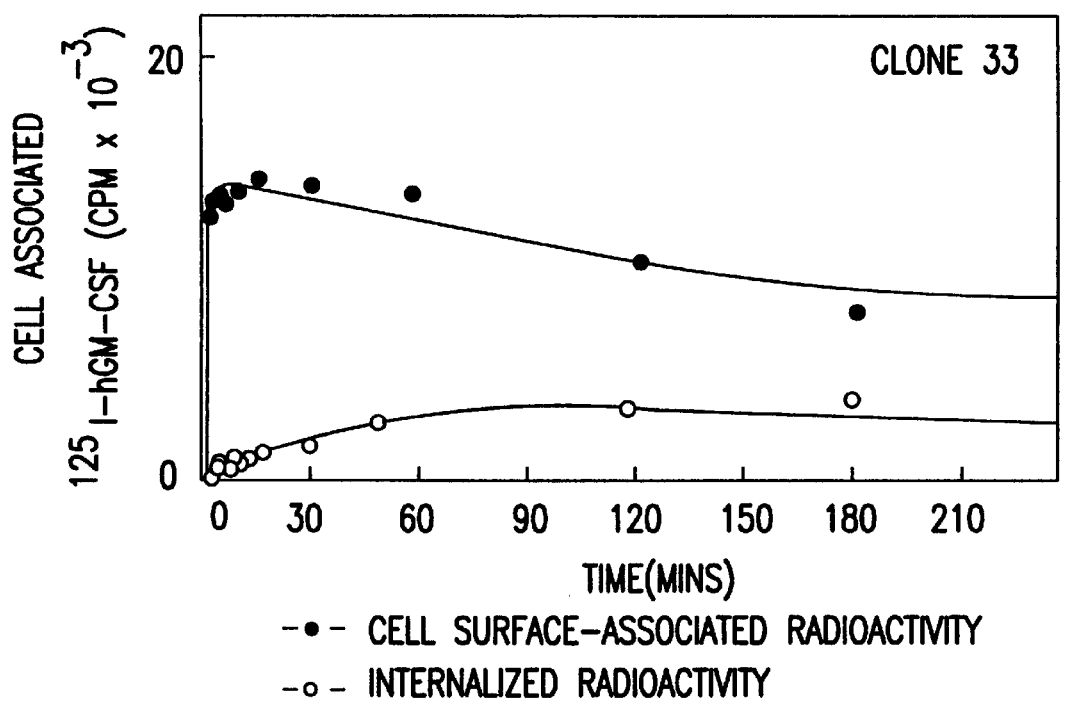
Figure 13B:
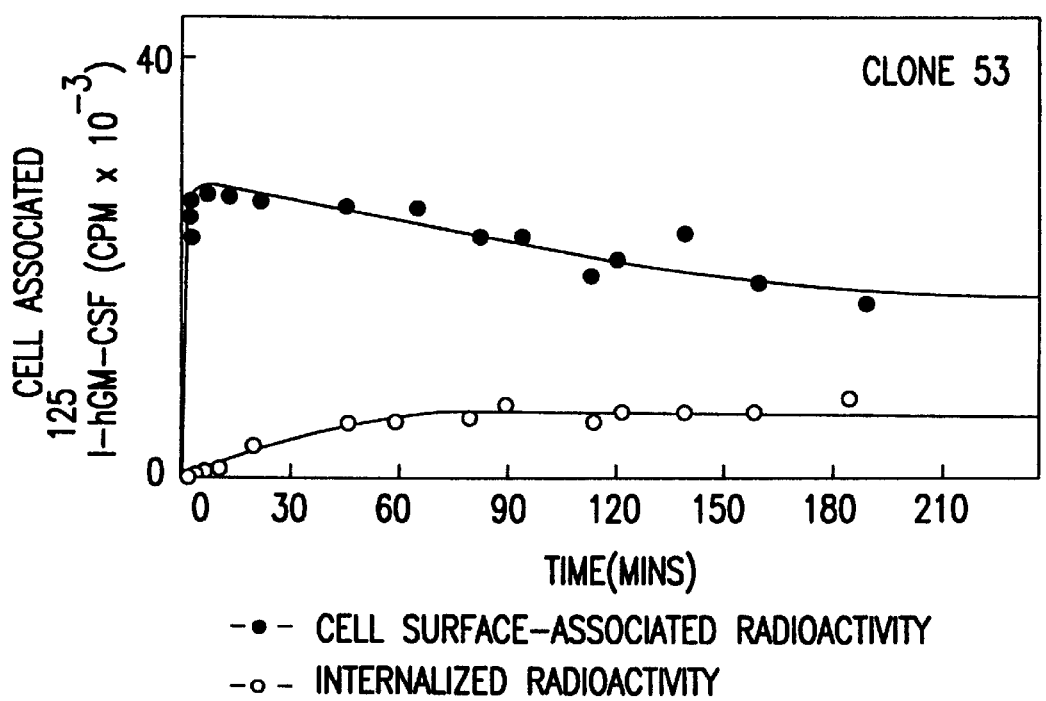

FIGS. 13A–B illustrate the internalization of $^{125}$I-hGM-CSF bound to hGM-R-FD clone 33 cells (FIG. 13A) or hGM-R-FD clone 53 cells (FIGS. 13A–B) at 37° C. The former cells had been maintained in a mixture of murine and human GM-CSF while the latter had been maintained in hGM-CSF only. The curves show the variation of cell surface associated and internalized radioactivity with time, after addition of $^{125}$I-hGM-CSF, determined as described (Nicola, N. A. et al., Growth Factors 1:41–49 (1988)); the lines through the experimental points (means of duplicate tubes) were fitted by computer as described by Nicola, N. A., supra. For clone 33, $1.9\times10^6$ cells were used per point and the $^{125}$I-hGM-CSF concentration was 13 nM, and for clone 53, $1.8\times10^6$ cells were used per point and the $^{125}$I-hGM-CSF concentration was 13 nM.

DETAILED DESCRIPTION OF THE PREFERRED EMBODIMENTS

The following abbreviations are used herein:

| | |
|---|---|
| h-, mGM-CSF | human or murine granulocyte-macrophage colony-stimulating factor |
| G-CSF | granulocyte colony-stimulating factor |
| multi-CSF | multipotential colony stimulating factor |
| IL-2 | interleukin-2 |
| HRF | hepes buffered (10 mM, pli 7.4) RPMI medium containing 10% v/v foetal calf serum |
| PBS | phosphate buffered saline |
| EDTA | ethylene diamine tetraacetic acid |
| FCS | foetal calf serum |
| IL-3 | interleukin-3 |
| IL-6 | interleukin-6 |
| EPO | erythropoietin |
| PRL | prolactin |
| h- | human |
| m- | murine |
| r- | rat |
| LIF | leukemia inhibitory factor |
| PCR | polymerase chain reaction |
| ORF | open reading frame |
| h-GH-R | human receptor for GM-CSF |
| h-GM-R-FD | FDC-PL cells tranfected with hGM-R |
| IL2R | IL-2 receptor (B chain) |
| IL6R | IL-6 receptor |
| GMR, GM-CSF-R | GM-CSF receptor |
| $K_D$ | equilibrium dissociation constant |
| EPOR | EPO receptor |
| PRLR | PRL receptor |
| SDS | sodium dodecyl sulphate |
| SSC | standard saline citrate |
| DNTP | deoxynucleoside triphosphate |
| DSS | disuccinimidyl suberate |

By "GM-CSF receptor" is meant a glycosylated or unglycosylated proteinaceous (i.e., amino acid containing) molecule comprising, in its entirety, an extracellular domain, a transmembrane domain and an intracytoplasmic tail. The receptor molecule is capable of specifically binding radioactively labeled GM-CSF or derivatives thereof, said binding being defined inter alia as being competed for by unlabeled GM-CSF.

By "recombinant GM-CSF receptor" is meant a glycosylated or unglycosylated polypeptide molecule, with or without other associated molecules (e.g., lipids), produced by recombinant means such as by the ligation of a cDNA molecule encoding the receptor or its derivative into an appropriate expression vector in the correct reading frame relative to a promoter, introducing the resultant recombinant expression vector into a suitable host and growing said host under conditions appropriate for the expression and, if necessary, transportation of the recombinant receptor or its derivative from said host, and then purifying the recombinant receptor or derivative.

By "GM-CSF-stimulation-sensitive cell" is meant a cell carrying a receptor to which GM-CSF can bind thereby causing the stimulation of proliferation or functional activation of that cell, as hereinbefore described. The term "bind" in relation to GM-CSF and its receptor is used in its broadest sense, and means any association between GM-CSF and its receptor, and particularly in relation to cell-bound receptor, sufficient to induce the stimulation of proliferation or functional activation of the cell on which the receptor is located. By "non-bound GM-CSF" is generally meant circulating GM-CSF.

By "substantial amino acid homology" or "substantial amino acid identity" is meant molecules having a sequence homology of approximately 75% or more, preferably greater than or equal to 85% and even more preferably greater than or equal to 90–95%.

"Cancer" is used in its broadest sense, and includes any cancer, tumor and/or leukemias en masse or as individual cells. "Aberrations" of bound GM-CSF receptor or its nucleotide sequence is used to mean any alteration in amino acid and/or nucleotide sequence detectable by analysis of the respective homologues as determined, for example, by hybridization studies. Accordingly, a cancer cell may contain an altered GM-CSF receptor detectable as being so altered by the use of the GM-CSF receptor or its encoding nucleotide sequence contemplated by the present invention.

General techniques for cloning and expressing cDNA are well known in the art, and can be found, for example, in Maniatis, T. et al., *Molecular Cloning: A Laboratory Manual*, Cold Spring Harbor Laboratory, Cold Spring Harbor, N.Y. (1982). For the purposes of exemplification only, the present invention is described with reference to the cDNA encoding a hGM-CSF receptor expressed in COS-7 cells employing the COS cell expression vector πH3M (Aruffo, A. and Seed, B., *Proc. Natl. Acad. Sci.* (*USA*) 84:8573–8577 (1987)). This is done with the understanding that the present invention includes within its scope cDNA encoding hGM-CSF receptor expressed in any vector and/or host. For example, it would be a matter of routine or not undue experimentation for a person skilled in the art to place the subject cDNA into a prokaryotic expression vector and express same in bacteria, such as *Escherichia coli*, Bacillus species or Pseudomonas species. Using routine experimentation, the cDNA can be expressed in eukaryotic cells such as yeasts, fungi, insect cell lines, mammalian cell lines other than COS cells, or plant cells. By known methods, the cDNA can also be transferred into germ line or somatic cells to form transgenic animals.

The present invention extends to single or double stranded DNA, cDNA or mRNA, wherein at least one nucleotide strand thereof encodes, or is complementary to, a nucleotide strand which encodes human GM-CSF receptor or its derivatives, and to any vector, expression or otherwise, containing same, including viral vectors.

In a preferred embodiment, the invention provides a recombinant DNA molecule comprising a gene encoding the human low-affinity GM-CSF receptor, or a homologue or derivative thereof which encodes a polypeptide having at least 75% sequence identity or homology with said receptor and/or which retains at least one-tenth of the relative binding affinity of the native human low-affinity GM-CSF receptor for human GM-CSF, said gene being operably linked to a promoter. More preferably said polypeptide comprises at least one of an extracellular domain, a transmembrane domain, and an intracellular domain.

Although the sequence presented in FIG. 6B refers specifically to the low-affinity GM-CSF receptor, the inventors have now discovered that the low affinity GM-CSF receptor itself forms a component of the high affinity GM-CSF receptor. The high-affinity GM-CSF receptor is therefore specifically included in the scope of the present invention.

In accordance with a particularly preferred embodiment of the present invention, there is provided the GM-CSF receptor molecule having at least a portion of the amino acid sequence shown in FIG. 6B (SEQ ID NO:6). This sequence is of a 400 amino acid polypeptide with a molecular weight of approximately 45,000, having a single hydrophobic transmembrane domain, a glycosylated extracellular domain and a short (54 amino acid) intracytoplasmic tail. The ligand-binding (or extracellular or soluble) domain (23-319) contains eleven cysteine residues. The subject receptor does not contain a tyrosine kinase domain, and does not show homology with members of the immunoglobulin gene superfamily, but does share sequence homology with receptors of other hemopoietic growth factors, such as human IL-6, erythropoietin arid IL-2 (β-chain). This GM-CSF receptor shows a single class of binding affinity ($K_D$=2–8 nM), with specificity for GM-CSF, but not IL-3.

It requires only routine experimentation for persons skilled in the art to construct a cDNA sequence encoding the receptor molecule comprising at least a portion of the amino acid sequence shown in FIG. 6B using methods which are well established and materials which are readily available, as described herein.

Given the aforementioned amino acid sequence and biochemical properties, the present invention includes within its scope a synthetic GM-CSF receptor molecule prepared by the chemical addition of amino acids by established techniques and in a sequence as established herein. The invention further includes recombinant or synthetic derivatives of GM-CSF receptor carrying single or multiple amino acid substitutions, deletions and/or additions to any or all regions or domains of the receptor molecules. Such derivatives may be functional (i.e., biological) equivalents with respect to their ability to bind to GM-CSF or its derivatives, and/or may exhibit substantial amino acid homology or identity to the aforementioned GM-CSF receptor amino acid sequence. One preferred derivative of GM-CSF receptor comprises all or part of the extracellular domain (soluble portion). Derivatives also include any or all of the receptor molecule in glycosylated or unglycosylated form. Depending upon the expression system and host employed, for example, the recombinant receptor may or may not be glycosylated. Both glycosylated and unglycosylated forms of the recombinant or synthetic GM-CSF receptor or its derivatives are within the scope of the present invention.

Functionally active derivatives or equivalents of the GM-CSF receptor can readily be identified using the methods described herein.

The invention is also directed inter alia to the cDNA encoding a GM-CSF receptor is hereinbefore defined. The cDNA comprises a nucleotide sequence shown in FIG. 6B (SEQ ID NO:4). The scope of the present invention includes cDNA derivatives carrying single or multiple nucleotide substitutions, deletions and/or additions relative to the aforementioned cDNA sequence. Such derivatives may encode the entire GM-CSF receptor molecule or derivatives thereof, such as a GM-CSF receptor carrying single or multiple amino acid substitutions, deletions and/or additions. The present invention also encompasses a cDNA carrying a nucleotide sequence substantially homologous to the subject nucleotide sequence, i.e., carrying at least 75% homology, preferably 80–85% homology and even more preferably greater than 90–95% homology. Methods for producing such derivatives, for example by site-directed mutagenesis, random mutagenesis, or enzymatic cleavage of the nucleic acid or protein and/or ligation of the nucleic acid, are well known in the art, as are methods for determining whether the thus-modified nucleic acid has significant homology or identity to the subject sequence, for example by hybridization.

The present invention further includes molecules such as polypeptides fused to the GM-CSF receptor or its derivatives, or nucleotide sequences contiguous to GM-CSF receptor-encoding sequences. For example, and not by way of limitation, it may be desirable to produce a fusion protein comprising GM-CSF receptor or its derivative and an amino acid sequence from another polypeptide or protein, examples of the latter, especially prokaryotic systems, being enzymes such as β-galactosidase, phosphatase, urease and the like. Most fusion proteins are formed by the expression of a recombinant gene in which two coding sequences have been joined together such that their reading frames are in phase. Alternatively, polypeptides can be linked in vitro by chemical means. All such fusion or hybrid derivatives of CM-CSF receptor or the respective encoding nucleotide sequences are encompassed by the present invention.

The present invention, therefore, provides recombinant and synthetic GM-CSF receptor and derivatives thereof in sufficient quantity for the development of, for example, receptor therapeutics and diagnostics.

Accordingly, another aspect of the invention contemplates a method for modulating the proliferation or functional activation of GM-CSF-stimulation-sensitive cells in a mammal which method comprises the administration to said mammal of an effective amount of GM-CSF receptor or its derivative for a time and under conditions sufficient to reduce the amount of non-bound GM-CSF. The subject method is predicated on the binding of GM-CSF circulating in the body to soluble receptor before the lymphokine can bind to the cell-bound receptor, thereby reducing the amount of GM-CSF available for binding to GM-CSF-stimulation-sensitive cells.

The invention extends to the use of the entire, or a portion of, a recombinant or synthetic GM-CSF receptor or its derivative in the modulation of proliferation or functional activation of GM-CSF-stimulation-sensitive cells, but preferably the soluble or extracellular domain (e.g., comprising at least a portion of amino acids 23-319 of SEQ ID NO:6) is used.

This method is particularly useful in treating disease states such as myeloid leukemias where the leukemic cells express GM-CSF receptors (Young, Y. G. and Griffin, J. D., *Blood* 68:1178–1181 (1986)). Many types of myeloid leukemia cells, for example, cannot undergo proliferation in vitro unless exogenous colony stimulating factors are available (Metcalf, D., *The Hemopoietic Colony Stimulating Factors*, Elsevier, Amsterdam (1984)). Accordingly, recombinant or synthetic GM-CSF receptor or its derivatives administered in vivo will bind to circulating GM-CSF and thus compete for binding of the latter to cell bound GM-CSF receptor. The subject method will also assist as therapeutic agents in abrogating the toxic effects of over-production of GM-CSF noted in animal model systems (Lang, R. A. et al., *Cell* 51:675–686 (1987); Johnson, G. R. et al., *EMBO J.* 8:441–448 (1989)).

The present invention also extends to antibodies (or fragments or derivatives thereof) and particularly monoclonal antibodies, to recombinant or synthetic GM-CSF receptor or its derivatives. Such antibodies are particularly useful in purifying GM-CSF receptors and for quantitating the same. The subject invention also extends to antibodies (monoclonal or polyclonal) against said first antibodies for the purposes of assaying plasma, serum or body fluids, cell surfaces or cell extracts for the presence of GM-CSF receptors. One or other of the aforementioned antibodies may be labelled with a reporter molecule for use, for example, in sandwich assays. Methods for production and screening of polyclonal and monoclonal antibodies, optionally including the use of adjuvants, methods for labelling such antibodies with radioactive, fluorescent, or chemical labels, and methods of immunoassay, such as radioimmunoassay, fluorescent immunoassay, and enzyme-linked immunoassay (ELISA), and coupling of antibodies to solid supports to form immunoadsorbents, are routine in the art.

Furthermore, the recombinant or synthetic GM-CSF receptors can be used in developing agonists and antagonists to augment or reduce binding of GM-CSF to its cell-bound receptors. For example, a transfected cell line bearing recombinant GM-CSF receptors may be used to screen compounds for such activities. The present invention extends to the use of such agonists or antagonists in the treatment of disease states caused by excessive or insufficient proliferation or functional activation of GM-CSF-stimulation-sensitive cells. Possible agonists or antagonists include naturally occurring or synthetic fragments of GM-CSF, as well as other naturally occurring or synthetic chemical compounds, which may be screened by the aforesaid method, using binding of labelled GM-CSF to the cells as a marker.

The present invention also extends to the use of GM-CSF or its derivatives in the manufacture of a medicament for the treatment of GM-CSF-related diseases. Such diseases include cancers, tumors and leukemias caused by, or associated with, GM-CSF-stimulation-sensitive cells.

Another aspect of the present invention extends to the use of recombinant or synthetic GM-CSF receptor or derivatives thereof, and particularly to nucleotide sequences encoding the same, in the diagnosis of cancers composed of, or associated with, GM-CSF-stimulation-sensitive cells by detecting cell-bound GM-CSF receptors or aberrations thereof, or nucleotide sequences encoding the same, in said cancer cells.

In accordance with the present invention, the functional, low-affinity hGM-CSF receptor has been cloned from placenta, and it has been shown that it recognizes only GM-CSF and not interleukin-3. This receptor, when transfected into COS cells, shows nearly identical low affinity to, and the same specificity as the receptor on placental membranes. Moreover, like the low affinity hGM-CSF receptor on hemopoietic cells, the transfected receptor is characterized by a rapid ligand dissociation rate ($T_{1/2}$=5 minutes) and poor internalization (approximately 10–20% after 2 hours at 37° C.).

Furthermore, as shown in FIGS. 9A–B, the positions of four cysteine residues are approximately conserved in the receptors for GM-CSF, IL-6, erythropoietin and IL-2 (β-chain) respectively, and the context in which three of these residues are found is identical between the four receptor types. These four cysteine residues, which might form pairs of intra-chain disulphide bonds, do not coincide with either of the two cysteine residues of the IL-6 receptor associated with the putative immunoglobulin domain structure (Yamasaki, K. et al., *Science* 241:825–828 (1988)).

Trp236 is conserved, and in three of the receptors is adjacent to an Arg residue. A further homology between all four receptor sequences is found just N-terminal of the transmembrane domain (FIGS. 9A–B). The consensus sequence starting at position 294 of the GM-CSF receptor (the "WS—WS" box) is found in all four receptors. The position of this sequence is close to the transmembrane domain in three of the receptors (for GM-CSF, erythropoietin-and IL-2 (β-chain)), but is further away in the IL-6 receptor.

A string based on the "WS—WS" box (VXXRXX$_{(6-11)}$ WSXWS) (SEQ ID NO:7) was used to search the most up-to-date database (Protein Research Foundation, Japan;

April 1989), and a region homologous to this string was found in the rat prolactin receptor (rPRL receptor; Boutin, J. M. et al., *Cell* 53:69–77 (1988)) just N-terminal to its transmembrane domain (FIGS. 9A–B). Strikingly, all four of the extracellular cysteine residues in the rPRL receptor, as well as a Lys-Trp doublet, are found in approximately the same relative positions as those of the four hemopoietic receptors; (FIG. 9A). The rPRL receptor also has a transmembrane cysteine residue (Boutin, J. M. et al., *Cell* 53:69–77 (1988)), but the transmembrane sequence is not homologous to the hGM-CSF receptor. By contrast, the "WS—WS" box is not found in a close relative of the prolactin receptor, the growth hormone receptor (Leung et al, 1988), which in other regions share 75–100% sequence similarity with the prolactin receptor (Boutin, J. M. et al., *Cell* 53:69–77 (1988)). The hGM-CSF receptor therefore appears to be a member of a new subset of growth and differentiation factor receptors, defined by the set of five receptors described above (i.e., hGM-CSF, hIL-6, murine EPO, hIL-2 (β-chain) and rPRL receptors).

In the GM-CSF receptor mRNA, there is a short 22 codon ORF prior to the long ORF encoding the GM-CSF receptor. Interestingly, such short ORFs are also found 5' of the main receptor coding region in the DNA sequences for the human IL-6 receptor (Yamasaki, K. et al., *Science* 241:825–828 (1988)), the murine IL-1 receptor (Sims, J. E. et al., *Science* 241:585–589. (1988)) and the human IL-2 receptor α and β-chains (Nikaido, T. et al., *Nature* 311:631–635 (1984); Hatekeyama, M. et al., *Science* 244:551–556 (1989)) and might act, if translated, to depress the translation of the main receptor coding regions. Such a mechanism might partly explain the low levels of expression of these receptors in normal cell types.

The present invention is further described by way of reference only to the following non-limiting examples:

EXAMPLE 1

Materials and Methods

The following materials or methods were employed in subsequent examples. Biological starting materials referred to herein are known in the art.

A cDNA library derived from poly-A+selected human placental RNA, constructed in the COS cell expression vector πH3M (Aruffo, A. and Seed, B., *Proc. Natl. Acad. Sci.* (USA) 84:8573–8577 (1987)) and consisting of approximately $5 \times 10^6$ independent clones, was provided by Dr. B. Seed (Massachusetts General Hospital, Boston, USA). Approximately 107 clones were produced by transforming MC1061/p3 cells, sorting them into 500 pools of approximately $2 \times 10^4$ clones, and preparing glycerol stocks. Miniprep DNA from each was transfected into COS-7 cells by electroporation. Briefly, $1.5 \times 10^6$ COS-7 cells in 180 μl phosphate-buffered saline pH7.3 (PBS) were mixed with 20 μl miniprep DNA (3 μg) and chilled on ice for 5 minutes. Cells were electroporated in 0.4 cm gap cuvettes at 300 V and 125 μFD ($t_c$=8.2–10.5 msec), returned to ice for 5 minutes and finally cultured in 2 ml Dulbecco's modified Eagle's medium (DME) containing 10% (v/v) foetal calf serum (FCS) in glass slide-based flaskettes (Lab-Tek, Nunc Inc., Naperville, USA). These conditions led to a 15–20% transfection frequency in surviving COS-7 cells as assessed by control transfections of ICAM/CDM8 (Simmons, D. et al., *Nature* 331:624–627 (1988) labeled with a radioiodinated anti-ICAM monoclonal antibody W-CAM-1 (Boyd, A. et al., *Proc. Natl Acad Sci.* (USA) 85:3095–3099 (1988)). After 48 hours, the medium was removed and the transfected monolayers assessed for binding of radioiodinated human GM-CSF ($4-8 \times 10^5$ cpm of $^{125}$I-GM-CSF (1–2 nM) in 1 ml Hepes buffered RPM1 medium pH7.2/10% FCS) for 60 minutes at 20° C. The monolayers were washed twice in medium, fixed in 2.5% (w/v) glutaraldehyde/PBS and dipped in 1% (w/v) gelatine as described (Nicola, N. A. and Metcalf, D., *J. Cell. Physiol.* 124:313–321 (1985)). The slides were dipped in Kodak NTB2 photographic emulsion at 42° C. and exposed in the dark for 48 hours at 4° C. in light-proof boxes containing dessicant. Slides were developed for 3 minutes in Kodak D19 developer (40 g/500 ml water), and rinsed in water and fixed for 3 minutes in Agfa G433C fixer before staining in 10% filtered Giemsa stain in water. Slides were screened at 10–20× magnification and two positive pools (#29 and #138) were selected. Corresponding glycerol stocks of *E. coli* transformants were partitioned into smaller pools until single cDNA clones able to cause COS-7 cells to bind $^{125}$I-GM-CSF were obtained.

Sequencing Strategy

The inserts and various internal fragments of clones 29 and 138 were subcloned into M13 vectors and sequenced by the dideoxy chain termination method (Sanger, F. et al., *Proc. Natl. Acad Sci.* (USA) 741:5463–5467 (1977)) using modified T7 polymerase (Tabor, S. and Richardson, C. C., *Proc. Natl. Acad. Sci.* (USA) 84:4767–4771 (1987); Sequenase, USB) and primers internal to subcloned segments. Ambiguities were resolved using dITP. Primers corresponding to some of these subclones were used to extend the sequence to adjacent segments. Both strands of clone 138 were sequenced in their entirety (average gel characters per contiguous character=4.87). All subcloning boundaries were resequenced on full-length clones. The mRNA-synonymous strand of clone 29 was completely sequenced, and ambiguities resolved using oligonucleotides on the opposite strand.

Analysis of RNA and DNA (Northern and Southern Blotting)

Cytoplasmic polyadenylated RNA (approximately 1.5 μg), prepared essentially as described by Gough, N. M., *Anal. Biochem.* 173:93–95 (1988), was fractionated on 1% (w/v) agarose gels containing 20 mM morpholinopropane sulphonic acid, 5 mM sodium acetate, 1 mM EDTA (pH 7.0), plus 6% (v/v) formaldehyde, and transferred to nitrocellulose. Prior to hybridization, filters containing RNA were soaked in 2×SSC containing 0.2% (w/v) Ficoll, 0.2% (w/v) polyvinylpyrollidone, 0.2% (w/v) bovine serum albumin, 2 mM sodium pyrophosphate, 1 mM ATP, 30 50 μg/ml denatured salmon sperm DNA and 50 μg/ml *E. coli* tRNA at 67° C. for several hours. Hybridization was performed in the same buffer plus 0.1% (w/v) SDS at 67° C. The hybridization probe was the gel-purified 1300bp Xho1-EcoRI fragment spanning the 5' end of cDNA clone pGMR138, radiolabelled to a specific activity of approximately $10^9$ cpm/μg by random priming (Feinberg, A. P. and Vogelstein, B., *Anal. Biochem.* 132:6–13 (1983)) and included in the hybridization at approximately $5 \times 10^7$ cpm/ ml. Filters were washed extensively in 2×SSC, 0.1% (w/v) SDS at 67° C. and finally in 0.2×SSC at 67° C. prior to autoradiography.

Ten μg aliquots of high molecular weight genomic DNA were digested with PstI, electrophoresed in 0.8% agarose gels and transferred to nitrocellulose. Conditions for hybridization and washing were as described above for RNA analysis. The hybridization probe was the gel-purified 786 bp Kpn-EcoRI fragment spanning the 3' end of the hGM-CSF receptor coding region, radiolabelled to a specific activity of approximately $2-4 \times 10^8$ cpm/μg by nick-translation and included in the hybridizations at approximately $2 \times 10^7$ cpm/ml.

RNA Detection Using the Polymerase Chain Reaction

RNA (approx. 1 μg) was subjected to first strand cDNA synthesis in a 20 μl reaction containing 50 mM Tris-Cl (pH 8.3 at 42° C.), 20 mM KCl, 10 mM MgCl$_2$, 5 mM dithiothreitol, 1 mM of each dNTP, 20 μg/ml oligo-dT and 20 units AMV reverse transcriptase (Boehringer Mannheim) for 40 minutes at 42° C. After completion of first-strand synthesis, the reaction was diluted to 100 μl with distilled water and 5 μl used for each PCR (polymerase chain reaction). Polymerase chain reactions contained 200 μM of each dNTP, 1 μM of each specific primer, buffer as supplied in the GeneAmp kit (Cetus Corp., USA) and 1.25 units Taq polymerase in a volume of 50 μl. The primers used for PCR were 5'-CTTCTCTCTAGACCAGCA (SEQ ID NO:1) (position 131-147) and 5'-ACATGGGTTCCTGAGTC (SEQ ID NO:2) (position 676-660) defining a 530 bp fragment. The PCR reaction conditions were: 2 minutes at 94° C.; 2 minutes at 65° C.; 3 minutes at 72° C. for 25 cycles in a Perkin-Elmer-Cetus DNA thermal cycler. A portion of the PCR reaction was electrophoresed through a 1.2% (w/v) agarose gel and transferred to nitrocellulose. Filters were prehybridized, hybridized and washed as described above. The hybridization probe was the gel-purified 1.9 kbp cDNA insert of pGMR138, radiolabelled to a specific activity of approximately $10^9$ cpm/μg by random priming and included in the hybridization at approximately $2 \times 10^7$ cpm/ml.

Radioligands

Purified, recombinant human or mouse GM-CSF produced in non-glycosylated form in *E. coli* (Delamarter, J. F. et al., *EMBO. J.* 4:2575–2581 (1985)) was radioiodinated by the modified iodine monochloride method of Nicola, N. A. et al., *Growth Factors* 1:41–49 (1988); briefly, 2 μg of protein (2 μl) was incubated with 1 m Ci Na $^{125}$I (New England Nuclear, Dreieich, W. Germany) in 40 μl of 0.2 M Na phosphate buffer pH 7.2 containing 0.2% (w/v) Tween 20. Iodine monochloride (0.03 mM in 2 M NaCl) was added in two lots of 3 μl and 6 μl while vortex-mixing the solution. The reaction mixture was passed through a column of Sephadex G-25M (Pharmacia, Uppsala, Sweden) to separate macromolecular radioactivity from free iodine (Hilton, D. J. et al., *Proc. Natl. Acad. Sci. (USA)* 85:5971–5975 (1989)). $^{125}$I-hGM-CSF was 100% bindable (Calvo, J. C. et al., *Biochem. J.* 212:259–264 (1983)) and displayed a specific radioactivity of 20,000–40,000 cpm/ng by the self-displacement analysis of Calvo, J. C. et al., *Biochem. J.* 212:259–264 (1983). $^{125}$I-mGM-CSF had specific radioactivity 120,000 cpm/ng and bindability 40–50%. Unlabelled and labelled (specific radioactivity 40,000 cpm/ng) human IL-3 was purchased from Amersham (Buckinghamshire, England).

Binding Experiments

HL60 cells grown for 5 days in DME medium/10% FCS containing 1.25% (w/v) dimethyl sulphoxide were resuspended at $5 \times 10^6$ cells/50 μl in Hepes (10 mM, pH 7.2) buffered RPMI medium (HR) containing 10% (v/v) foetal calf serum (HRF). Fifty μl aliquots of cells were incubated with increasing concentrations of $^{125}$I-hGM-CSF (0–2 nM) with or without unlabelled hGM-CSF (0.3 pm) at 4° C. for 4 hours. Cell suspensions were then layered over 180 μl chilled foetal calf serum and centrifuged for 5 minutes at 700 g in small plastic centrifuge tubes and the cell pellet removed by cutting the tube with a scalpel blade. Cell-associated and free radioactivity were separately determined by counting duplicate tubes in a gamma-counter. Transfected COS-7 cells were harvested 48–72 hours after transfection by removing the supernatant and incubating the adherent cells in 40 mM EDTA in HR containing 200 μg/ml chondroitin sulphate, and incubating at 37° C. for a further 40 minutes (Padmanabhan, R. et al., *Anal. Biochem.* 170:341–348 (1988)). The detached and disaggregated cells were centrifuged at 700 g for 5 minutes and resuspended in HRF with or without 20 mM EDTA and 100 pg/ml chondroitin sulphate. Saturation binding isotherms or competition experiments were performed as for HL60 cells. Human placental membranes were prepared from fresh term placentas essentially as described by Yeung, Y. G. et al., *Proc. Natl. Acad. Sci. (USA)* 84:1268–1271 (1987), with 6 g of placenta yielding 4 ml of membrane suspension. For each binding point, 40 μl of membrane suspension was mixed with 40 μl HRF and increasing concentrations of $^{125}$I-hGM-CSF with or without excess unlabeled hGM-CSF (0.3 μM). After 1 hour incubation at 20° C. the membranes were centrifuged at 30,000 g for 5 minutes, the supernatant removed with a fine Pasteur pipette and membrane pellets and supernatants counted separately in a gamma-counter.

Saturation binding of $^{125}$I-hGM-CSF to hGM-R-FD cells and Scatchard transformations were performed as described above, using an incubation time of 1 hour at 20° C. Cross-modulation of hGM-CSF receptors by mGM-CSF and of multi-CSF or mGM-CSF receptors by hGM-CSF was performed as described by Walker, F. et al, *Cell* 45:269–276 (1985), with preincubation time of 30 minutes at 37° C. followed by binding times of 3 hours at 0° C. Receptor internalization studies were performed at the indicated concentrations of $^{125}$I-hGM-CSF, and the data were analyzed by curve fitting of the experimental points (Nicola, N. A. et al., *Growth Factors* 1:41–49 (1988)).

Cross-linking Experiments

Binding of $^{125}$I-hGM-CSF to cells in solution was performed at 4° C. as described above, and the cell pellets resuspended in 1 ml of ice-cold Na phosphate buffered (20 mM, pH 7.2) saline (0.15 M). Disuccinimidyl suberate (Sigma, Mo., USA) in anhydrous acetonitrile (10 μl) was immediately added to give a final concentration of 0–1 mM, and the cells incubated for 15 minutes on ice before centrifuging the cell pellet at 13,000 g for 1 minute. The cell pellet was treated with DNAase in the presence of protease inhibitors and prepared for sodium dodecyl sulphate polyacrylamide gel electrophoresis as described (Nicola, N. A. and Peterson, L., *J. Biol. Chem.* 261:12384–12389 (1986)).

Analysis of Binding Data

Specific binding was determined as the difference between binding in the absence or presence of excess unlabeled hGM-CSF. Specifically bound cpm were converted to molar concentrations using the specific radioactivity of $^{125}$I-GM-CSF determined by self-displacement analysis. Curve-fitting of the binding data was performed using the LIGAND program of Munson, P. J. and Robard, D., *Anal. Biochem.* 107:220–239 (1980) before conversion to the Scatchard transformation. Two binding site fits were used only if the fit to the data was significantly improved ($p<0.05$) over the one binding site fit.

Production and Selection of hGM-R Retrovirus

A 1.7 kbp Xho1 fragment containing the insert cDNA of pGMR29, prepared as described herein, was inserted into the Xho1 site of pJZen2(SVNeo), a derivative of the retroviral vector pMPZen (Johnson, G. R. et al., *EMBO J.* 8:441–448 (1989)) in which a multiple cloning site has replaced the single Xho1 site of pMPZen, and a 1.7 kbp neomycin-resistance expression cassette (the BamHI-E corI fragment of pDol (Korman, A. J. et al., *Proc. Natl. Acad. Sci. (USA)* 84:2150–2154 (1987)), blunt-ended and ligated to ClaI linkers) was inserted into the ClaI site (J. Chang, O. Bernard and K. Klingler, unpublished data). ψ2 packaging cells (Mann, R. et al., *Cell* 33:153–159 (1983)) were electroporated with pJZen2 (SVNeo)-hGM-R DNA as previously described (Johnson, G. R. et al., *EMBO J.* 8:441–448 (1989)), and transfectants were selected 2 days later using 400 µg/ml of antibiotic G418 (Geneticin, Sigma). G418-resistant 2 clones were selected for high surface expression of hGM-R by binding of $^{125}$I-hGM-CSF. Retroviral titres of receptor-positive ψ2 clones were tested by polybrene-mediated infection of NIH3T3 fibroblasts (Cepko, C. L. et al., *Cell* 37:1053–1062 (1984)). The clone selected for further work (ψ2-GMR) had a titre of $1.2 \times 10^4$ viral particles/ml.

Derivation of Infected FDC-P1 Cell Lines

Adherent ψ2-GMR cells ($3 \times 10^6$ per 75 cm$^2$ flask) were irradiated (35 Gy), and co-cultured with $10^6$ FDC-P1 cells (Dexter, T. M. et al., *J. Exp. Med.* 152:1036–1047 (1980)) in 20 ml Delbecco's Modified Eagle's Medium (DMEM) with 10% foetal calf serum (FCS) and 10% pokeweed-mitogen stimulated spleen cell conditioned medium. Washed supernatant cells from 48 hour cocultures were cultured in agar-medium at a density of 300 cells/ml with either $10^3$ U/ml of mGM-CSF, $6 \times 10^3$ U/ml of hGM-CSF, or a combination of both. After 3 days incubation, clones developing in mGM-CSF had achieved 50–100 cells in size. In contrast, fewer clones had developed in cultures stimulated by hGM-CSF; these were dispersed in morphology, and most contained only 10–30 cells. Individual clones growing in cultures stimulated by hGM-CSF were removed using a micropipette, and cloned cell lines established and maintained in 1 ml cultures of DMEM with 20% FCS containing either $6 \times 10^5$ U/ml hGM-CSF (12 lines) or $6 \times 10^3$ U/ml hGM-CSF plus $10^3$ U/ml mGM-CSF (36 lines). Subcloning of individual cell lines was performed by growing colonies in agar medium cultures of 200 cells/ml then removing individual colonies after 7 days of incubation and continuing culture of these colonies in suspension.

Agar Cultures

These were performed in 35 mm plastic Petri dishes (Nunc, Adelaide) using 1 ml of agar medium (DMEM with final concentrations of 20% FCS and 0.3% agar) (Metcalf, D., *The Hemopoietic Colony Stimulating Factors*, Elsevier, Amsterdam (1984)) and 300 cultured cells.

The stimuli used for colony formation were purified recombinant mGM-CSF (specific activity $3 \times 10^8$ U/mg protein) or purified recombinant hGM-CSF (specific activity $10^8$ U/mg protein) produced as nonglycosylated derivatives in *E. coli*. These were included as 0.1 ml volumes during preparation of the agar cultures, and serial twofold dilutions were performed using 5% FCS in 0.95% saline. Mean cell numbers in 7-day colonies were determined by pooling 30–50 sequential colonies.

EXAMPLE 2

Detection of High and Low Affinity GM-CSF Receptors

Figure 1A:
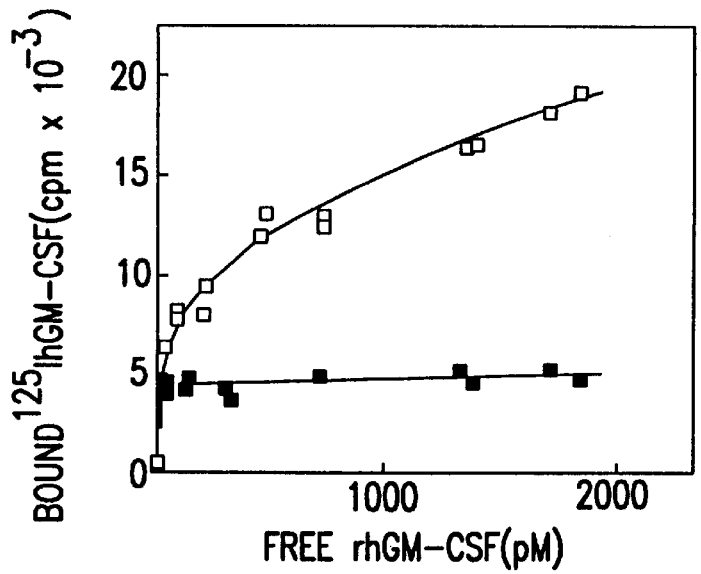
FIGS. 1A–D show saturation binding isotherms and Scatchard analysis of $^{125}$I-hGM-CSF binding to either (FIGS. 1A, 1C) HL60 cells after incubation in 1.25% (w/v) DMSO for 5 days or (FIGS. 1B, 1D) purified human placental membranes.
Figure 1B:
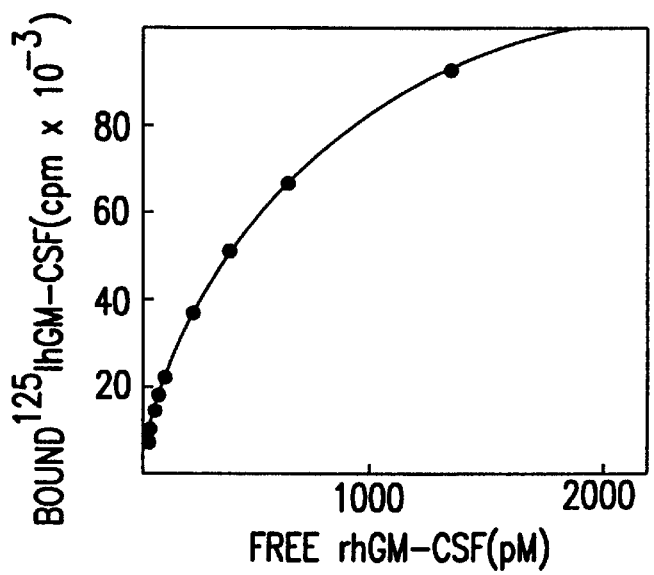
Figure 1C:
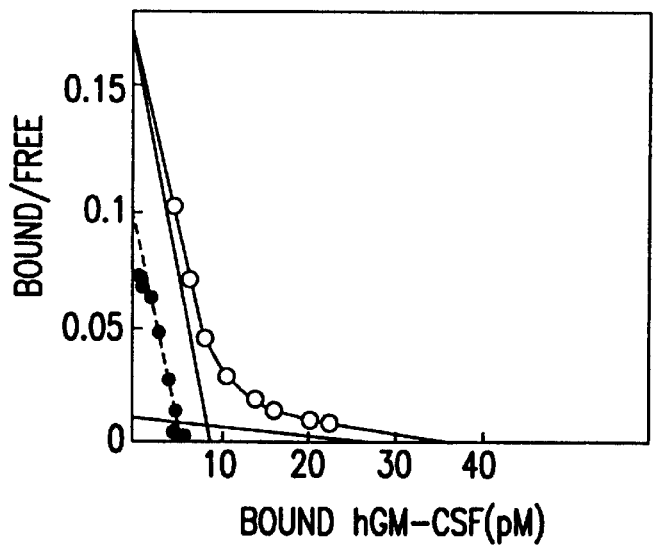

In accordance with the methods described herein, both high and low affinity GM-CSF receptors were detected on human bone marrow cells, primary human myeloid leukemic cells and the human promyelocytic leukemic cell line, HL-60 (FIGS. 1A, 1C). FIGS. 1A, 1C shows the saturation binding isotherm at 4° C. for $^{125}$I-hGM-CSF binding to HL-60 cells that had been induced to differentiate for 5 days in 1.25% (w/v) dimethylsulphoxide (DMSO). Transformation of this data by the method of Scatchard (1949) after curve-fitting using the LIGAND program of Munson, P. J. and Robard, D., *Anal. Biochem.* 107:220–239 (1980) indicated that two, rather than one, binding sites were required to fit the data (p<0.05), with the high affinity receptors (40/cell) having a $K_D$ of 46 pM and the low affinity receptors (130/cell) having a $K_D$ of 2.9 nM. After allowing the same cells to dissociate bound GM-CSF for 10 minutes at 4° C. and determining the remaining bound $^{125}$I-hGM-CSF on the cells, only high affinity binding sites could be detected (FIGS. 1A, 1C). This indicates that the low affinity receptors display a more rapid rate of ligand dissociation than do high affinity receptors. This may explain the failure of other investigators (Gasson, J. C. et al., *Proc. Natl. Acad. Sci.* (*USA*) 83:669–673 (1986); Park, L. L. et al., *J. Exp. Med.* 164:251–262 (1986); Kelleher, C. A. et al., *Leukemia* 2:211–215 (1988)) to detect the low affinity receptors, since the subject binding procedure involves a rapid, single-step separation of cell-bound from free ligand. These authors described a single affinity class of GM-CSF receptors, having $K_D$ of 20–600 pM, on human hemopoietic cells.

Figure 1D:
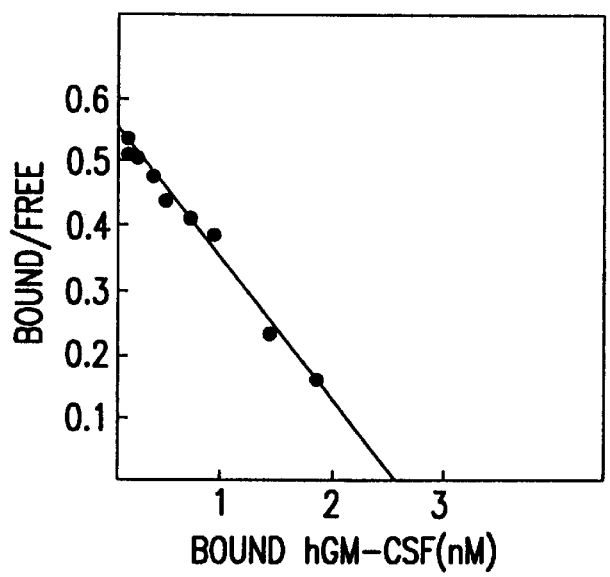
Figure 2A:
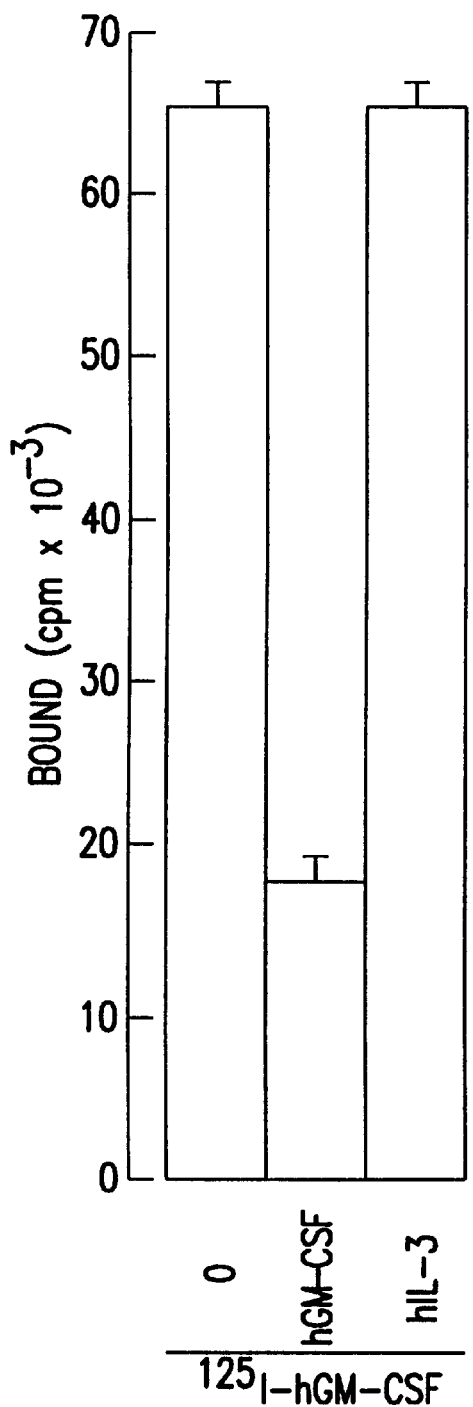
FIGS. 2A–B show the binding specificity of hGM-CSF (2A) and hIL-3 (2B) receptors on human placental membranes. Membranes (40 $\mu$l) were incubated in duplicate with $^{125}$I-hGM-CSF (200,000 cpm in 110 $\mu$l HRF) with or without unlabelled hGM-CSF (500 ng) or h-IL-3 (100 ng) for 1 hour at 20° C. Similarly, 40 $\mu$l membranes were incubated with $^{125}$I-h-IL-3 (220,000 cpm in 110 $\mu$l HRF)
Figure 2B:
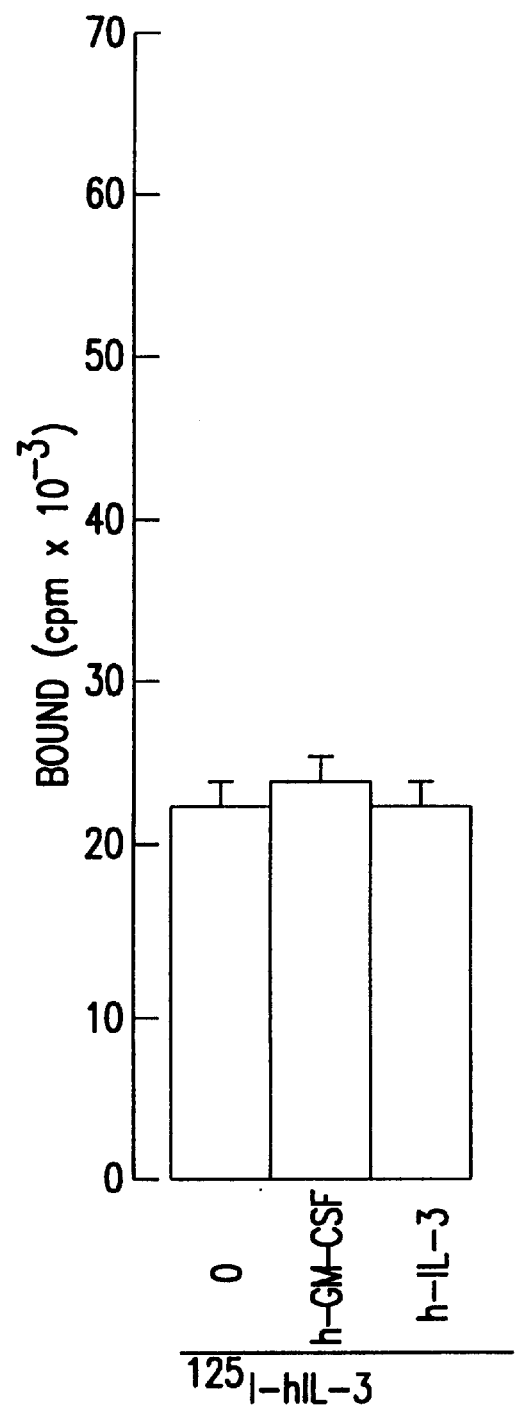

Specific binding of hGM-CSF to purified human placental cell membranes was detected (FIGS. 1B, 1D), but this binding was to a single class of low-affinity receptors ($3 \times 10^9$ receptors/mg placenta, $K_D$=4.6 M). The human placental GM-CSF receptor appeared to recognize only hGM-CSF and not hIL-3 (FIGS. 2A–B). Moreover, no hIL-3 receptors were detected on human placental membranes (FIGS. 2A–B).

EXAMPLE 3

Cloning and Expression of Human GM-CSF Receptor

In order to clone the GM-CSF receptor, an expression screening strategy was employed in simian COS cells. The low abundance of the GM-CSF receptor in all cell sources so far examined necessitated the screening of large cDNA libraries and consequent sensitive detection of positive transfected cells. The detection procedure we have adopted involves binding $^{125}$I-hGM-CSF to transfected COS cells grown on glass microscope slides, followed by direct autoradiography. This screening approach has two major advantages over previous receptor cloning procedures which used radioiodinated ligand as their detection tool (Sims, J. E. et al., *Science* 241:585–589 (1988); D'Andrea, A. D. et al., *Cell* 57:277–285 (1989)). First, this procedure is extremely sensitive, since single clones could be detected from pools of $2 \times 10^4$ clones (c.f. 1 in $10^3$, D'Andrea, A. D. et al., *Cell* 57:277–285 (1989); 1 in 350, Sims, J. E. et al., *Science* 241:585–589 (1988)). Secondly, the procedure allows easy identification of artifacts due to non-specific binding, which would otherwise have made identification of a single GM-CSF-receptor positive cell on a slide containing approximately $10^6$ negative COS cells impossible.

A human placental cDNA library of approximately $5 \times 10^6$ independent recombinants in a COS cell expression vector (Aruffo, A. and Seed, B., *Proc. Natl. Acad. Sci.* (*USA*) 84:8573–8577 (1987)) was sub-fractionated into 500 pools of approximately $2 \times 10^4$ clones each, and DNA from each pool was separately transfected into $1.5 \times 10^6$ COS cells by electroporation. The cells were cultured for 48 hours on glass slides, incubated with a relatively high concentration of $^{125}$I-hGM-CSF (approximately 2 nM), fixed and then dipped in liquid photographic emulsion. The slides were developed and individually examined microscopically; positive cells were identified by the presence of autoradiographic grains. Of the first 250 pools screened, two gave rise to 1 or 2 positive cells (pools 29 and 138) (FIGS. 3A–D). One of these pools (138) was partitioned into smaller pools (20 pools of 1500 recombinants then 60 pools of 80 recombinants and finally 200 single clones), with autoradiographic screening at each stage, until a single cDNA clone was obtained which could transfer high capacity $^{125}$I-hGM-CSF-binding to COS cells. Following three rounds of selection in COS cells, the individual cDNA clone in a second positive pool of DNA (pool 29) was ultimately identified as coding for the GM-CSF receptor by colony hybridization with the 1.8 kbp insert of clone pGMR138. Plasmids encoding the cDNA inserts of clones 29 and 138 were designated pGMR29 and pGMR138 respectively.

EXAMPLE 4

Analysis of Cloned GM-CSF Receptor

The binding of $^{125}$I-hGM-CSF to the transfected receptor on COS cells was specific, since it could be competed for by unlabelled hGM-CSF but not by murine GM-CSF (which has no activity on human cells), or by human IL-3, G-CSF or IL-6 (FIGS. 3A–E).

Figure 4D:
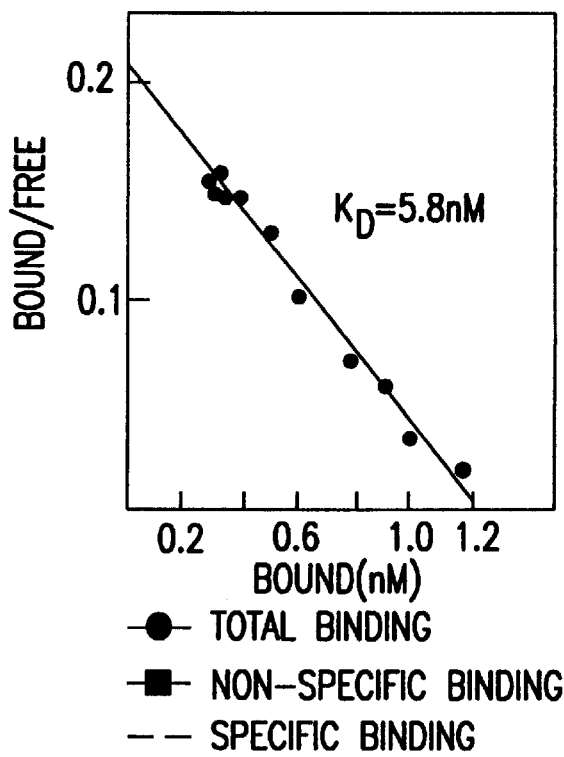

The binding characteristics of the cloned GM-CSF receptor (clone 138; Example 3) when transfected to COS cells are shown in FIGS. 4A–D. The saturation binding isotherm for $^{125}$I-hGM-CSF binding to transfected COS cells at 20° C. showed a single class of binding site with an equilibrium dissociation constant of 6.8 nM and 600,000 receptors per cell. In contrast, untransfected COS cells or COS cells transfected with vector alone showed no significant binding at these cell concentrations (3–7×10$^4$ cells/point). Autoradiographic analyses indicated that only about 20% of the transfected cells were receptor positive (reflecting the transfection efficiency), so that positively transfected cells probably displayed about 3×10$^6$ receptors per cell, compared with a reported value of 1700 receptors per cell for untransfected COS cells (Cocita Baldwin, G. et al, *Blood* 73:1033–1037 (1989)). Displacement of $^{125}$I-hGM-CSF by unlabelled hGM-CSF also demonstrated only a single class of receptor with K$_D$=5.8 nM, and this binding was not displaced by unlabelled hIL-3 (FIGS. 4B, 4D). The similar binding affinities observed when labelled or unlabelled hGM-CSF was varied indicates that iodination did not significantly alter the binding affinity of hGM-CSF for this receptor. In several different experiments binding of $^{125}$I-hGM-CSF to transfected COS cells was determined in suspension (in binding medium with or without 20 mM EDTA and 100 μg/ml chondroitin sulphate to prevent cell aggregation), or on adherent cells. The apparent K$_D$ varied from 4–8 nM, indicating that neither calcium nor adherence significantly altered the binding characteristics of the transfected receptor.

EXAMPLE 5

Molecular Size

The molecular size of the hGM-CSF receptor on HL60 cells and transfected COS cells was determined by chemical cross-linking with disuccinimidyl suberate(DSS) (FIG. 5). As observed by others (DiPersio, J. et al., *J. Biol. Chem.* 263:1834–1840 (1988)), the GM-CSF receptor on HL-60 cells had an approximate Mr of 85,000, so that cross-linking with $^{125}$I-hGM-CSF (Mr=15,000) gave an Mr of 100,000. Both before and after rapid ligand dissociation (with or without low affinity binding, respectively—see FIGS. 1A–D), a major cross-linked band of Mr 100,000 and a minor cross-linked band of Mr 95,000 (representing receptors of Mr 85,000 and 80,000, respectively) were seen; these may represent different glycosylation variants of a single binding subunit. Cross-linking of $^{125}$I-hGM-CSF to the transfected receptor on COS cells gave a major band of similar molecular weight (90,000–110,000), although it was somewhat broader than that seen on HL-60 cells, possibly reflecting more variable glycosylation. Similar cross-linking gels run under reducing conditions gave the same cross-linked receptor molecular weight, indicating that the mature receptor was not comprised of disulphide-linked subunits.

EXAMPLE 6

Sequence Analysis

The inserts of clones 29 and 138 were subcloned and sequenced by standard techniques. In the composite sequence shown in FIGS. 6B–D, clone 29 is represented by nucleotides 1–1709 and clone 138 by nucleotides 7–1807. The two sequences are otherwise identical, except for a single silent base difference (G->A) in clone 29 at position 1148. Each sequence encodes a large open reading (ORF) frame of 400 amino acids preceded by a short ORF of 22 amino acids. The methionine codon beginning the larger reading frame is in a context which corresponds well to the consensus sequence (RCC<u>ATG</u>G) for translation initiation sites (Kozak, M., *Nucl. Acids Res.* 12:857–872 (1987)), while the shorter ORF begins with a methionine codon in poor context. The large ORF begins with a presumed signal peptide sequence of 22 amino acids, and residue Glu23 is assigned to the first amino acid of the mature protein by comparison with typical signal peptide cleavage sites (von Heijne, G., *Nucl. Acids Res.* 14:4683–4690 (1986)).

The predicted 378 amino acid mature GM-CSF receptor is calculated to have a molecular weight of 43,728, which is approximately half the size of the receptor observed by cross linking of $^{125}$I-hGM-CSF to HL60 cells and to COS-7 cells transfected with clone pGMR138 (FIG. 5). This difference between the predicted size of the core receptor polypeptide and the mature receptor on cells is probably due to the attachment of carbohydrate to the 11 potential N-linked glycosylation sites in the putative 297 amino acid extracellular domain, since we have shown that the mature receptor does not contain disulphide-linked subunits. A hydrophobicity plot (FIG. 7) suggests that a stretch of 27 uncharged amino acids extending from Gly320 to Phe346 (FIGS. 6B–D) (SEQ ID NOS:4 and 6) represents a transmembrane domain. This putative transmembrane domain is followed by a 54 amino acid intracellular domain which begins with a short stretch of basic amino acids, a feature common to the cytosolic face, next to the membranespanning segments, of many transmembrane proteins. The 54 amino acid intracellular domain of the GM-CSF receptor shares no apparent homology with that of the IL6-R.

In the 3'-untranslated region of the GM-CSF-receptor mRNA there is a sequence element homologous to the "Alu" family of repetitive elements (residues 1493 to 1760) which make up approximately 3% of the human genome (Jelinek, W. R. and Schmid, S. W., *Ann. Rev. Biochem.* 51:813–844 (1982)). Further downstream there are two poly A addition signals immediately prior to the poly A tail (FIG. 6A).

The predicted GM-CSF binding extracellular domain (amino acids 23–319) contains eleven cysteine residues, but these do not appear to form disulphide loops characteristic of receptors of the immunoglobulin superfamily (Sims, J. E. et al., *Science* 241:585–589 (1988); Yamasaki, K. et al., *Science* 241:825–828 (1988)). The short intracellular domain (54 amino acids) may serve a role in signal transduction. This domain has no apparent sequence homology with the catalytic domain of any growth factor receptor known to be a tyrosine kinase (Hanks, S. K. et al., *Science* 241:42–52 (1988)). However, direct comparison of the GM-CSF receptor with that of the human IL-6 receptor (Yamasaki, K. et al., *Science* 241:825–828 (1988)) revealed significant homology (FIG. 9B). The positions of four cysteine residues are approximately conserved (GM-CSF-R $C_{126}$, $C_{136}$, $C_{165}$, $C_{178}$ vs. IL6-R $C_{121}$, $C_{132}$, $C_{165}$, $C_{176}$), and these do not coincide with the two cysteine residues ($C_{47}$ and $C_{96}$) of the IL-6 receptor associated with the immunoglobulin-like domain (Yamasaki, K. et al., *Science* 241:825–828 (1988)). Furthermore, there are patches of homology in the intracellular domain (FIGS. 9A–B) and a perhaps surprising similarity between the transmembrane domains of the two receptors (GM-CSF-R $L_{33}$-$L_{342}$ vs. IL6-R $L_{374}$-$L_{386}$), including in each case the transmembrane cysteine residue. The particular conservation of residues in the transmembrane regions may suggest a common ability to associate with other transmembrane proteins or lipids in their respective membranes. Indeed, a similarly placed cysteine residue in the transmembrane region of the Semliki Forest virus El spike protein, corresponding to the middle of the inner leaflet of the membrane, has been shown to be a site of palmitoylation (Schmidt, M. et al., *J. Biol. Chem.* 263:18635–18639 (1988)). However, the position of the intramembrane cysteine residue relative to the putative inner face of the membrane (represented by $R_{388}$ (IL6-R) and $K_{347}$ (GM-CSF-R)) differs between the two receptors, so if this residue is functionally or structurally important it may play a different role for each receptor.

The extracellular domain of the hGM-CSF receptor shows homology not only to that of the IL-6 receptor but also to those of the receptors for erythropoietin (D'Andrea, A. D. et al., *Cell* 57:277–285 (1989)), interleukin-2 (Hatekeyama, M. et al, *Science* 244:551–556 (1989)), rat prolactin (Boutin, J. M. et al, *Cell* 53:69–77 (1988)) interleukin-4 (Mosley, B. et al., *Cell* 59:335–348 (1989)) and interleukin-3 (Itoh, N. et al., *Science* 247:324–327 (1990)). The regions of homology include the four cysteine residues mentioned above and a short amino acid sequence centered around the sequence Trp-Ser-X-Trp-Ser (SEQ ID NO:3) near the transmembrane region (FIG. 9B).

Prior to the long ORF encoding the GM-CSF receptor is a short ORF. This potentially encodes a polypeptide, although since its initiation methionine is in a context unrelated to the consensus sequence for good translation initiation (see above) this reading frame may not be translated (Kozak, M., *Cell* 44:283–292 (1986)). Such short ORFs 5' of the main receptor coding region are found in the hIL6 receptor cDNA (Yamasaki, K. et al., *Science* 241:825–828 (1988)), and one of these (25 nucleotides upstream) in fact begins with a methionine codon in a context that is stronger than that which was assigned to begin the hIL6 receptor precursor. This suggests that these short ORFs might act to depress the translation of the main receptor coding regions.

EXAMPLE 7

The GM-CSFReceptor Transcript

Since the cDNA clone pGMR138 was isolated from a human placental cDNA library, we tested whether or not mRNA corresponding to this transcript was also present in hemopoietic cells known to express the GM-CSF receptor. Northern blot analysis (e.g., FIG. 8A) revealed that H-60 cells, which are known to express high-affinity GM-CSF receptors, contain a 2.1 kb transcript hybridizing at high stringency to the pGRM138 probe (tracks 3–5), whereas CEM T-lymphoblastoid cells and HepG2 hepatocellular carcinoma cells contain no detectable transcript hybridizing with this probe (tracks 1 and 2).

Owing to the low abundance of this RNA species, a more sensitive survey of RNA from various hemopoietic and nonhemopoietic cells was undertaken, using PCR-based amplification of cDNA corresponding to various RNAs. Such analyses (e.g., FIG. 8B) revealed the presence of GM-CSF receptor transcripts in a variety of human myeloid cell lines, including HL-60, U937 and AML193, but not in CEM T-lymphoid, Raji Burkitt lymphoma nor Hep G2 hepatic cells. Interestingly we have found that HeLa cells also display GM-CSF receptors, and have transcripts corresponding to this cDNA clone (FIG. 8B).

EXAMPLE 8

Introduction of hGM-CSF Receptor into Murine Cells

When the cloned low-affinity receptor for human GM-CSF from placental cells, described above, is introduced into a murine GM-CSF-dependent hemopoietic cell line (FDC-P1) using a retroviral vector, it retains its low-affinity phenotype but can nevertheless transmit the biological signals required for cell proliferation.

The murine FDC-P1 hemopoietic cell line used does not proliferate in cultures containing $10^6$ Units/ml of hGM-CSF, and no cells survive in such cultures. In four separate cocultivation experiments with 2 cells producing the hGM-CSF receptor retrovirus, 0.3 to 1% of FDC-P1 cells were able to proliferate clonally in agar cultures stimulated by hGM-CSF. Cloned cell lines (hGM-R-FD lines) were developed from individual colonies and maintained using either a high concentration of hGM-7CSF, or a mixture of mGM-CSF with a lower concentration of hGM-CSF.

Southern blot analysis of DNA from 19 such hGM-R-FD lines (FIG. 10a, tracks 2–20) revealed the presence of a single viral integrant in each clone, except clone 57 in which two integrants were evident (track 19). With the exception of clones 50 and 52, which are potentially siblings (tracks 13 and 14), the viral integration sites differed in each cloned line, as revealed by the different sizes of hybridizing DNA fragments, confirming the independent clonal origin of each line.

EXAMPLE 9

Differences between Cell Lines Maintained in Human GM-CSF versus Murine plus Human GM-CSF At 25–39 days after the establishment of the cloned lines, a comparative analysis of 19 of these lines, chosen at random, revealed distinctive differences between the two types of lines in their behaviour in clonal cultures (FIGS. 11A–B).

The parental FDC-P1 cell line usually exhibits a cloning efficiency in agar-medium of 60–100% when stimulated by mGM-CSF, forming large, tight, colonies. hGM-R-FD lines maintained in hGM-CSF usually exhibited lower clonogenic potential (42±17%), and total colony numbers were similar in cultures stimulated by h or mGM-CSF (FIGS. 11A–B). The colonies characteristically had an irregular shape or were wholly dispersed, and maximal colony size was relatively small. Colony size was typically 2–4 times larger in parallel cultures stimulated by mGM-CSF. (For nine cell lines, mean colony size with mGM-CSF was 530±340 cells, versus 240±110 with hGM-CSF).

When hGM-R-FD cell lines maintained in murine plus human GM-CSF were stimulated by hGM-CSF, the frequency of clonogenic cells was even lower (15±15%) than that of lines maintained in hGM-CSF alone, although the morphology of the colonies was similar. With increasing duration of maintenance in the mixture of m+hGM-CSF, a progressive fall occurred in the frequency of clonogenic cells responsive to hGM-CSF alone. In sharp contrast, when cells of these lines were stimulated by mGM-CSF, the frequency of clonogenic cells was much higher (96±21%). The morphology and size of these colonies resembled those of parental FDC-P1 cells, and there was a more than tenfold difference between the size of colonies stimulated by m or hGM-CSF. For ten cell lines mean colony size with mGM-CSF was 1900±880 cells, versus 170±130 with hGM-CSF.

EXAMPLE 10

Responsiveness to GM-CSF of Lines Maintained in Human versus Human plus Murine GM-CSF The dose-response curves of hGM-R-FD lines responding to stimulation by h or mGM-CSF indicated that responsiveness to hGM-CSF was 500–1000-fold lower than to mGM-CSF (FIGS. 11A–B, Table 1). Cell lines grown using hGM-CSF were twofold more responsive to hGM-CSF than cell lines maintained in a mixture of m+hGM-CSF, although both types exhibited a similar responsiveness to mGM-CSF (FIGS. 11A–B, Table 1).

TABLE 1

Quantitative Responsiveness of Cloned hGM-R FD Cell Lines to Stimulation by Murine or Human GM-CSF and Their Capacity to Bind Human GM-CSF.

|  | Units Needed to Stimulate 50% Maximal Colonies | | $^{125}$I-Human GM-CSF Bound per $10^6$ Cells |
| --- | --- | --- | --- |
| Line No. | mGM-CSF | hGM-CSF | (cpm) |
| Maintained in Murine plus Human GM-CSF | | | |
| 1 | 30 | 10,000 | 12,000 |
| 21 | 20 | 20,000 | 2,200 |
| 33 | 30 | 10,000 | 7,700 |
| 34 | 30 | 18,000 | 6,700 |
| 11 | 30 | 20,000 | 17,200 |
| 6 | 15 | 20,000 | 7,600 |
| 24 | 20 | 20,000 | 14,100 |
| 13 | 15 | — | 6,900 |
| 10 | 40 | 40,000 | 15,800 |
| 8 | 15 | 40,000 | 600 |
| Maintained in Human GM-CSF Alone | | | |
| 54 | 20 | 10,000 | 9,300 |
| 53 | 20 | 10,000 | 9,000 |
| 58 | 7 | 7,000 | 11,800 |
| 49 | 20 | 10,000 | 73,400 |
| 50 | 15 | <5,000 | 14,200 |
| 55 | 15 | 10,000 | 12,200 |
| 56 | 60 | 30,000 | 10,100 |
| 52 | 50 | 7,000 | 29,600 |
| 57 | 20 | 8,000 | 15,700 |
| Control FDC-P1 Cells | | | |
|  | 15 | — | 0 |
|  | 15 | — |  |
|  | 15 | — |  |

TABLE 1-continued

Quantitative Responsiveness of Cloned hGM-R FD Cell Lines to Stimulation by Murine or Human GM-CSF and Their Capacity to Bind Human GM-CSF.

|  | Units Needed to Stimulate 50% Maximal Colonies | | $^{125}$I-Human GM-CSF Bound per $10^6$ Cells |
| --- | --- | --- | --- |
| Line No. | mGM-CSF | hGM-CSF | (cpm) |

Three hundred cells were added to duplicate cultures containing increasing twofold concentrations of mouse or human GM-CSF. Colony counts were performed on day 7 and GM-CSF concentration stimulating 50% maximal colony numbers determined from each titration curve. Binding of $^{131}$I-labeled human GM-CSF determined in parallel using $5 \times 10^6$ cells.

EXAMPLE 11

Display of hGM-CSF Receptors on Transfected FDC-P1 Cells

Different cloned hGM-R-FD lines were assessed for their capacity to specifically bind $^{125}$I-hGM-CSF and, whilst all of them showed significant binding, there was considerable variation in the extent of this binding (Table 1). Clones maintained continuously in hGM-CSF alone showed higher average levels of binding than clones maintained in a mixture of hGM-CSF and mGM-CSF (Table 1).

Despite the variation in binding of $^{125}$I-hGM-CSF to different hGM-R-FD clones, saturation binding analysis and Scatchard transformation of the binding data showed similar binding affinities (slopes of the Scatchard transformation, $K_D$=4–6 nM) for all clones examined (FIGS. 12A–D). This binding affinity was of a single low-affinity class and was the same as for receptors on human placental membranes, transfected COS-7 cells, and retrovirally-infected 2 clones.

The binding of hGM-CSF at concentrations up to 1 µg/ml to the transfected receptor in hGM-R-FD clones for 30 minutes at 37° C. did not affect the subsequent binding of $^{125}$I-mGM-CSF to the native mGM-CSF receptor co-expressed on these cells. Similarly, the binding of mGM-CSF or m Multi-CSF at concentrations up to 0.5 µg/ml to their native receptors on hGM-R-FD cells at 37° C. did not affect the subsequent binding of $^{125}$I-hGM-CSF to the transfected hGM-CSF receptor.

When $^{125}$I-hGM-CSF was incubated with hGM-R-FD cells at 37° C. it rapidly associated with cell surface GM-CSF receptors and was then slowly internalized into the cells. The binding and internalization kinetics were essentially identical for hGM-R-FD clones maintained in m or hGM-CSF (FIGS. 13A–B). However, the internalization rate of occupied hGM-CSF receptors ($k_e$) was slower in hGM-R-FD cells ($k_e$=0.0042 minutes$^{-1}$) than on human HL60 cells ($k_e$=0.061 minutes$^{-1}$) and on occupied murine GM-CSF receptors on FDC-P1 cells ($k_e$=0.056 minutes$^{-1}$) (Nicola, N. A. et al., *Growth Factors* 1:41–49 (1988)).

After retrovirally-mediated transfection of murine hemopoietic FDC-P1 cells with a cDNA encoding the low-affinity human placental GM-CSF receptor, cell-surface hGM-CSF receptors were displayed at a level of $10^4$–$10^5$ per cell as a single binding class of low affinity ($K_D$=4–6 nM). Despite careful analysis, no high-affinity binding was detected, yet the transfected cells could internalize the hGM-CSF receptor (albeit at a rate 10 times slower than for endogenous mGM-CSF receptors), and acquired the capacity to proliferate in response to hGM-CSF. The quantitative responsiveness of hGM-R-FD cells to hGM-CSF was 500–1000-fold lower than to mGM-CSF, but determination of the binding constants suggests that occupied hGM-CSF or mGM-CSF receptors might be equally efficient in transducing proliferative signals in murine FDC-P1 cells. Firstly, the transfected hGM-CSF receptor binds hGM-CSF with a 100-fold lower affinity ($K_D$=5 nM) than that of the endogenous high-affinity receptor for mGM-CSF ($K_D$=50 pM) (Walker, F. and Burgess, A. W., *EMBO J.* 4:933–939 (1985)). Secondly, the 10-fold slower internalization rate of occupied hGM-CSF receptors compared to occupied mGM-CSF receptors at 37° C. implies that the apparent steady-state "affinity constants" will differ by a further factor of 10 (Nicola, N. A. et al., *Growth Factors* 1:41–49 (1988)).

EXAMPLE 12

Evolution of Recloned Sublines

Analysis of colonies grown from hGM-R-FD cell lines using m+hGM-CSF showed them to contain a major population of cells responsive only to mGM-CSF and a minor population responsive to hGM-CSF; this latter population rapidly diminished if colonies were grown for one week using only mGM-CSF. Colonies grown from cell lines maintained using hGM-CSF alone retained a stable content of clonogenic cells responding to either type of GM-CSF.

Cells from nine sublines-derived from mGM-CSF-stimulated lines and maintained exclusively in mGM-CSF usually formed colonies only when stimulated by mGM-CSF (cloning efficiency 68±24%), and the colonies formed were of uniformly large size. Cells from 13 sublines, also derived from m+hGM-CSF-stimulated cultures but then maintained in human GM-CSF, formed relatively small numbers of colonies (cloning efficiency 37±25%) of medium size in cultures stimulated by h or mGM-CSF, with maintenance of the characteristic 2 to 4-fold size difference between the two types of colony.

In tests on six cloned sublines derived from hGM-CSF-stimulated lines and maintained in hGM-CSF, 50±26% of the clonogenic cells were able to form colonies in cultures containing 800 ng/ml antibiotic G418. In contrast, clonogenic cells from six cloned sublines maintained using mGM-CSF were uniformly unable to form colonies in the presence of G418. This suggested that transcription of the inserted neomycin resistance gene was not maintained when cells were stimulated solely by mGM-CSF.

Southern blot analysis of DNA from a series of mGM-CSF-responsive and human-responsive sublines of primary line 21 revealed that in all subclones both the content and context of the hGM-R viral integrant were maintained (e.g., FIG. 10A, tracks 21–27), confirming the common derivation of these lines, despite their divergent biological properties, and suggesting that the lack of both hGM-CSF responsiveness and display of cell surface hGM-CSF receptors was not due to loss of the hGM-R construct.

RNA from six sublines maintained with mGM-CSF contained no detectable hGM-R viral transcripts (FIG. 10B, tracks 2–7), compared with abundant hGM-R viral transcripts evident in sublines maintained with hGM-CSF (tracks 8–11 and other data not shown), suggesting that the alteration in such cells was at the transcriptional or immediately post-transcriptional level.

Thus the behaviour of cloned hGM-R-FD cell lines differed, depending on whether they were maintained in hGM-CSF alone or a mixture of hGM-CSF and mGM-CSF. The former cell lines maintained a stable phenotype with equal clonogenicity in hGM-CSF or mGM-CSF, but clonogenicity was significantly lower than for cell lines maintained in mGM-CSF. The cell lines maintained in a mixture of mGM-CSF and a low concentration of hGM-CSF showed a progressive loss of cells able to respond to stimulation by hGM-CSF.

The behaviour of cell lines maintained in hGM-CSF was not influenced by the site of viral integration. The selection pressure exerted by culture with hGM-CSF alone maintained a constant level of expression of both viral genes (hGM-CSF-R and neoR), receptor expression and quantitative responsiveness to hGM-CSF. However, the low clonogenicity and colony size exhibited by these cells suggested the continuous generation within lines maintained in hGM-CSF of progeny cells that had lost responsiveness to hGM-CSF. In the absence of any other stimulus, these cells irreversibly lost proliferative potential and could not be rescued by subsequent culture in mGM-CSF. This phenomenon was confirmed by analysis of subcloned hGM-R-FD lines maintained in the presence of mGM-CSF only. Such subcloned lines maintained their viral inserts, but expression of both hGM-CSF receptor and neoR genes declined progressively to zero with increasing time in culture. The reasons for the relatively high frequency at which the viral genes were turned off are unclear, but this clearly did not depend on viral integration site. Indeed, suppression of retroviral expression has been observed in a variety of different cells, including murine hemopoietic cells (Chang, J. M. W. et al., *Mol. Cell. Biol.* 7:854–863 (1987); Magli, M-C. et al., *Proc. Natl. Acad. Sci.* (*USA*) 84:789–793 (1987); Emerman, M. and Temin, H. M., *Cell* 39:459–467 (1984)); the SV40 early region promoter, used in the present construct to drive the neomycin resistance gene, has been shown to be particularly sensitive to trans- and cis-acting negative regulatory factors (Chang, J. M. W. et al., *Mol. Cell. Biol.* 7:854–863 (1987); Magli, M-C. et al., *Proc. Natl. Acad. Sci.* (*USA*) 84:789–793 (1987); Emerman, M. and Temin, H. M., *Cell* 39:459–467 (1984); Gorman, C. M. et al., *Cell* 42:519–526(1985); Williams, D. A. et al., *Proc. Natl. Acad. Sci.* (*USA*) 83:2566–2570 (1986)).

The observation that the human placental GM-CSF receptor stimulated the proliferation of murine hemopoietic FDC-P1 cells lends support to the suggestion that this receptor subunit may form a component of the human GM-CSF receptor on hemopoietic cells. It also demonstrates that a low affinity GM-CSF receptor of nonhemopoietic origin can transduce proliferative signals and be internalized in a hemopoietic cell, in a ligand-dependent manner, in the absence of any high-affinity binding component. Indeed, since biological responsiveness of the transfected FDC-P1 cells was almost the same to m or hGM-CSF on a receptor occupied basis, this further suggests that the signalling components of both h- and mGM-CSF receptors may be highly conserved, and that the main function of high affinity subunits might be solely to increase the rate of receptor internalization and to increase the responsiveness of hemopoietic cells to low external concentrations of GM-CSF. Alternative interpretations of the data involving interaction or cointernalization of the introduced hGM-CSF receptor with endogenous mGM-CSF or Multi-CSF receptors were excluded.

Despite the conservation of signalling between human and murine GM-CSF receptors, there is no functional conservation in the GM-CSF-binding domain, and there was no conversion of the hGM-CSF receptor to a high-affinity receptor by interaction with the mouse cells that displayed high-affinity mGM-CSF receptors. The relationship of the cloned low-affinity hGM-CSF receptor to high-affinity GM-CSF receptors remains unclear. It is still possible that high-affinity GM-CSF receptors are unrelated to the low affinity hGM-CSF receptor. However, if, as we have postulated, the low affinity subunit can be converted to a high-affinity receptor by interaction with an "adaptor" subunit, then this interaction seems not to occur across these species.

A wide variety of potential therapeutic, diagnostic and preparative applications of GM-CSF receptors of this invention is envisaged, including, but not limited to, the following:

1. Inhibition of the growth of GM-CSF dependent myeloid leukemias,
2. Treatment of patients who have been overdosed with GM-CSF.
3. Local treatment of adverse side-reactions in patients receiving GM-CSF.
4. Control of systemic or local GM-CSF levels in patient with over-exuberant or inappropriate inflammatory responses.
5. Reduction of inflammatory response in patients with chronic infections (e.g., pulmonary fungal infections, listeriosis, tuberculosis, acute respiratory distress syndrome), autoimmune reactions or inappropriate GM-CSF production.
6. Classification of myeloid leukemias for stratification for outcome and selection for therapy.
7. Detection of aberrant expression of GM-CSF-R in tumours to allow selection of patients to receive combination therapy with GM-CSF and chemotherapy (exclusion of cancers with GM-CSF-R) (e.g., lung, breast and bladder cancer, myeloid leukemias).
8. Screening of patients with capacity to respond to GM-CSF in aplastic anemias and congenital neutropenias.
9. Identification of disease states mediated by autoimmune anti-GM-CSF-R antibodies (e.g., autoimmune neutropenias).
10. Preparation of affinity matrices to allow rapid purification of GM-CSF for clinical studies and therapeutic use.
11. Screening of potential agonists and antagonists of GM-CSF action, including antibodies.
12. Preparation of antibodies against the hGM-CSF-R to be used in:
    a. identification and quantitation of circulating soluble GM-CSF-R,
    b. screening marrow cells for evaluation prior to therapy
    c. evaluating marrow reserve in pre-treatment patients,
    d. determining pharmacokinetics of GM-CSF-R in clinical trials of GM-CSF-R.
13. Preparation of anti-idiotypic antibodies to mimic the action of GM-CSF for use in therapy and in lowering systemic lipid levels.
14. Preparation of nucleic acid probes for identification aberrant GM-CSF receptor genes in disorders such as myeloid leukemia.

Although these applications are listed with reference to hGM-CSF, it will be apparent to the person skilled in the art that corresponding veterinary diagnostic, therapeutic and preparative applications of appropriate animal GM-CSF-Rs are within the scope of the invention.

References cited herein are listed on the following pages. It will be clearly understood that the invention in it general aspects is not limited to the specific details.

REFERENCES

Aruffo, A. and Seed, B., *Proc. Natl. Acad. Sci. (USA)* 84:8573–8577 (1987)
Boyd, A. et al., *Proc. Natl. Acad Sci. (USA)* 85:3095–3099 (1988)
Boutin, J. M. et al., *Cell* 53:69–77 (1988)
Bussolino, F. et al., *Nature* 337:471–473 (1989)
Calvo, J. C. et al., *Biochem. J.* 212:259–264 (1983)
Cepko, C. L. etal., *Cell* 37:1053–1062 (1984)
Chang, J. M. W. et al., *Mol. Cell. Biol.* 7:854–863 (1987)
Cocita Baldwin, G. et al., *Blood* 73:1033–1037 (1989)
D'Andrea, A. D. et al., *Cell* 57:277–285 (1989)
Dedhar, S. et al., *Proc. Natl. Acad. Sci. (USA)* 85:9253–9257 (1988)
Delamarter, J. F. et al., *EMBO. J.* 4:2575–2581 (1985)
Dexter, T. M. et al., *J. Exp. Med.* 152:1036–1047 (1980)
DiPersio, J. et al., *J. Biol. Chem.* 263:1834–1840 (1988)
Donohue, R. E. et al., *Nature* 321:827–875 (1986)
Elliot, M. J. et al., *Blood* 74:2349–2359 (1989)
Emerman, M. and Temin, H. M., *Cell* 39:459–467 (1984)
Evans, D. B. et al., *Biochem. Biophys. Res. Commun.* 160:588–595 (1989)
Feinberg, A. P. and Vogelstein, B., *Anal. Biochem.* 132:6–13 (1983)
Gasson, J. C. et al., *Proc. Natl. Acad. Sci. (USA)* 83:669–673 (1986)
Gesner, T. G. et al., *J. Cell. Physiol.* 136:493–499 (1988)
Gorman, C. M. et al, *Cell* 42:519–526 (1985)
Gough, N. M., *Anal. Biochem.* 173:93–95 (1988)
Gough, N. M. and Nicola, N. A., in *Colony-Stimulating Factors: Molecular and Cellular Biology*, Hexter, T. M. et al, eds., Marcel Dekker, New York, pp. 111–153 (1989)
Gough, N. M. et al., *Nature* 309:763–767 (1984)
Hanks, S. K. et al., *Science* 241:42–52 (1988)
Hatekeyama, M. et al., *Science* 244:551–556 (1989)
Hilton, D. J. et al., *Proc. Natl. Acad. Sci. (USA)* 85:5971–5975 (1989)
Hopp, T. P. and Woods, K. R., *Mol. Immunol.* 20:483–489 (1983)
Itoh, N. et al., *Science* 247:324–327 (1990)
Jelinek, W. R. and Schmid, S. W., *Ann. Rev. Biochem.* 51:813–844 (1982)
Johnson, G. R. et al., *EMBO J.* 8:441–448 (1989)
Kelleher, C. A. et al., *Leukemia* 2:211–215 (1988)
Korman, A. J. et al., *Proc. Natl. Acad. Sci. (USA)* 84:2150–2154 (1987)
Kozak, M., *Cell* 44:283–292 (1986)
Kozak, M., *Nucl. Acids Res.* 12:857–872 (1987)
Lang, R. A. et al., *Cell* 51:675–686 (1987)
Lopez, A. F. et al., *Proc. Natl. Acad. Sci. (USA)* 86:7022–7026 (1989)
Magli, M-C. et al., *Proc. Natl. Acad Sci. (USA)* 84:789–793 (1987)
Maniatis, T. et al., *Molecular Cloning: A Laboratory Manual*, Cold Spring Harbor Laboratory, Cold Spring Harbor, N.Y. (1982)
Mann, R. et al., *Cell* 33:153–159 (1983)
Metcalf, D., *The Hemopoietic Colony Stimulating Factors*, Elsevier, Amsterdam (1984)
Metcalf, D. et al., *Blood* 55:138–147 (1980)
Metcalf, D. et al., *Exp. Hematol.* 15:1–9 (1987)
Morstyn, G. et al., *Trends Pharmacol. Sci.* 10:154–159 (1989)
Mosley, B. el al., *Cell* 59:335–348 (1989)
Munson, P. J. and Robard, D., *Anal. Biochem.* 107:220–239 (1980)
Nicola, N. A., *Immunol. Today* 8:134–139 (1987)

Nicola, N. A. and Metcalf, D., *J. Cell. Physiol.* 124:313–321 (1985)
Nicola, N. A. and Peterson, L., *J. Biol. Chem.* 261:12384–12389 (1986)
Nicola, N. A. et al., *Growth Factors* 1:41–49 (1988)
Nikaido, T. et al., *Nature* 311:631–635 (1984)
Padmanabhan, R. et al., *Anal. Biochem.* 170:341–348 (1988)
Park, L. L. et al., *J. Biol. Chem.* 261:4177–4183 (1986a)
Park, L. L. et al., *J. Exp. Med.* 164:251–262 (1986b)
Park, L. S. et al., *J. Biol. Chem.* 264:5420–5427 (1989)
Rettenmier, C. W. et al., *J. Clin. Invest.* 77:17401–1746 (1986)
Sanger, F. et al., *Proc. Natl. Acad. Sci. (USA)* 741:5463–5467 (1977)
Scatchard, G., *Ann. N.Y. Acad. Sci.* 51:660–672 (1949)
Schmidt, M. et al., *J. Biol. Chem.* 263:18635–18639 (1988)
Simmons, D. et al., *Nature* 331:624–627 (1988)
Sims, J. E. et al., *Science* 241:585–589 (1988)
Tabor, S. and Richardson, C. C., *Proc. Natl. Acad. Sci. (USA)* 84:4767–4771 (1987)
von Heijne, G., *Nuc. Acids Res.* 14:4683–4690 (1986)
Wegmann, T. G. et al., *Transplant. Proc.* 21:566–568 (1989)
Walker, F. and Burgess, A. W., *EMBO J.* 4:933–939 (1985)
Walker, F. et al., *Cell* 45:269–276 (1985)
Williams, D. A. et al., *Proc. Natl. Acad. Sci. (USA)* 83:2566–2570 (1986)
Wong, G. G. et al., *Science* 228:810 (1985)
Yamasaki, K. et al., *Science* 241:825–828 (1988)
Yeung, Y. G. et al., *Proc. Natl. Acad. Sci. (USA)* 84:1268–1271 (1987)
Young, Y. G. and Griffin, J. D., *Blood* 68:1178–1181 (1986)

What is claimed is:

1. An antibody or an antigen-binding fragment thereof which binds to a polypeptide having the amino acid sequence of SEQ ID NO:6.

2. An antibody or an antigen-binding fragment thereof which binds to a polypeptide having the amino acid sequence of residues 1–22 of SEQ ID NO:6.

3. An antibody or an antigen-binding fragment thereof which binds to a polypeptide having the amino acid sequence of residues 2–22 of SEQ ID NO:6.

4. An antibody or an antigen-binding fragment thereof which binds to a polypeptide having the amino acid sequence of residues 23–319 of SEQ ID NO:6.

5. An antibody or an antigen-binding fragment thereof which binds to a polypeptide having the amino acid sequence of residues 294–310 of SEQ ID NO:6.

6. An antibody or an antigen-binding fragment thereof which binds to a polypeptide having the amino acid sequence of residues 320–346 of SEQ ID NO:6.

7. An antibody or an antigen-binding fragment thereof which binds to a polypeptide having the amino acid sequence of residues 331–344 of SEQ ID NO:6.

8. An antibody or an antigen-binding fragment thereof which binds to a polypeptide having the amino acid sequence of residues 347–400 of SEQ ID NO:6.

9. A pharmaceutical composition comprising:
   1. an antibody or an antigen-binding fragment thereof according to any one of claims 1–8, and
   2. a pharmaceutically-acceptable carrier or diluent.

* * * * *

UNITED STATES PATENT AND TRADEMARK OFFICE
CERTIFICATE OF CORRECTION

PATENT NO. : 6,136,957
DATED : October 24, 2000
INVENTOR(S) : Nicola et al.

Page 1 of 1

It is certified that error appears in the above-identified patent and that said Letters Patent is hereby corrected as shown below:

<u>Title page,</u>
Item [54], please delete "Macrophane" and insert therein -- Macrophage --.

Item [63], please delete "which is a continuation of application No. 08/351,149" and insert therein -- "which is a division of 08/351,149 --.
Item [63], please delete "which is a division of application No. PCT/AU90/00342" and insert therein -- which is the national stage of PCT/AU90/00342 --.

Signed and Sealed this

Sixth Day of November, 2001

Attest:

*Nicholas P. Godici*

*Attesting Officer*

NICHOLAS P. GODICI
*Acting Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: both
      (D) TOPOLOGY: both (xi) SEQUENCE DESCRIPTION: SEQ ID NO:1:

CTTCTCTCTA GACCAGCA                                                   18

(2) INFORMATION FOR SEQ ID NO:2:

(i) SEQUENCE CHARACTERISTICS:
      (A) LENGTH: 17 base pairs
      (B) TYPE: nucleic acid
      (C) STRANDEDNESS: both
      (D) TOPOLOGY: both (xi) SEQUENCE DESCRIPTION: SEQ ID NO:2:

ACATGGGTTC CTGAGTC                                                    17

(2) INFORMATION FOR SEQ ID NO:3:

(i) SEQUENCE CHARACTERISTICS:
      (A) LENGTH: 5 amino acids
      (B) TYPE: amino acid
      (D) TOPOLOGY: both (xi) SEQUENCE DESCRIPTION: SEQ ID NO:3:

Trp Ser Xaa Trp Ser
1               5

(2) INFORMATION FOR SEQ ID NO:4:

(i) SEQUENCE CHARACTERISTICS:
      (A) LENGTH: 1808 base pairs
      (B) TYPE: nucleic acid
      (C) STRANDEDNESS: both
      (D) TOPOLOGY: both (ix) FEATURE:
      (A) NAME/KEY: CDS
      (B) LOCATION: 25..90

-continued

```
    (ix) FEATURE:
         (A) NAME/KEY: CDS
         (B) LOCATION: 150..1349

(xi) SEQUENCE DESCRIPTION: SEQ ID NO:4:

AGCAGGTGGA AGGAGAGGAA GCGG ATG CCG TGG GGT TTA CAG CAG GAA AAT          51
                          Met Pro Trp Gly Leu Gln Gln Glu Asn
                            1               5

CCG TGG AGA CAG CAG ATC CGA GAA GCG GCG ATG TTT GCG TAGAACCCTG         100
Pro Trp Arg Gln Gln Ile Arg Glu Ala Ala Met Phe Ala
 10              15                  20

TACGTGCTTC CTTCGGCCTG TCGCTCTTCC CTTCTCTCTG ACCAGCACC ATG CTT          155
                                                      Met Leu
                                                        1

CTC CTG GTG ACA AGC CTT CTG CTC TGT GAG TTA CCA CAC CCA GCA TTC        203
Leu Leu Val Thr Ser Leu Leu Leu Cys Glu Leu Pro His Pro Ala Phe
          5                  10                  15

CTC CTG ATC CCA GAG AAA TCG GAT CTG CGA ACA GTG GCA CCA GCC TCT        251
Leu Leu Ile Pro Glu Lys Ser Asp Leu Arg Thr Val Ala Pro Ala Ser
     20              25                  30

AGT CTC AAT GTG AGG TTT GAC TCC AGG ACG ATG AAT TTA AGC TGG GAC        299
Ser Leu Asn Val Arg Phe Asp Ser Arg Thr Met Asn Leu Ser Trp Asp
 35              40                  45                  50

TGC CAA GAA AAC ACA ACC TTC AGC AAG TGT TTC TTA ACT GAC AAG AAG        347
Cys Gln Glu Asn Thr Thr Phe Ser Lys Cys Phe Leu Thr Asp Lys Lys
              55                  60                  65

AAC AGA GTC GTG GAA CCC AGG CTC AGT AAC AAC GAA TGT TCG TGC ACA        395
Asn Arg Val Val Glu Pro Arg Leu Ser Asn Asn Glu Cys Ser Cys Thr
              70                  75                  80

TTT CGT GAA ATT TGT CTG CAT GAA GGA GTC ACA TTT GAG GTT CAC GTG        443
Phe Arg Glu Ile Cys Leu His Glu Gly Val Thr Phe Glu Val His Val
              85                  90                  95

AAT ACT AGT CAA AGA GGA TTT CAA CAG AAA CTG CTT TAT CCA AAT TCA        491
Asn Thr Ser Gln Arg Gly Phe Gln Gln Lys Leu Leu Tyr Pro Asn Ser
             100                 105                 110

GGA AGG GAG GGT ACC GCT GCT CAG AAT TTC TCC TGT TTC ATC TAC AAT        539
Gly Arg Glu Gly Thr Ala Ala Gln Asn Phe Ser Cys Phe Ile Tyr Asn
115                 120                 125                 130

GCG GAT TTA ATG AAC TGT ACC TGG GCG AGG GGT CCG ACG GCC CCC CGT        587
Ala Asp Leu Met Asn Cys Thr Trp Ala Arg Gly Pro Thr Ala Pro Arg
             135                 140                 145

GAC GTC CAG TAT TTT TTG TAC ATA CGA AAC TCA AAG AGA AGG AGG GAG        635
Asp Val Gln Tyr Phe Leu Tyr Ile Arg Asn Ser Lys Arg Arg Arg Glu
             150                 155                 160

ATC CGG TGT CCT TAT TAC ATA CAA GAC TCA GGA ACC CAT GTG GGA TGT        683
Ile Arg Cys Pro Tyr Tyr Ile Gln Asp Ser Gly Thr His Val Gly Cys
             165                 170                 175

CAC CTG GAT AAC CTG TCA GGA TTA ACG TCT CGC AAT TAC TTT CTG GTT        731
His Leu Asp Asn Leu Ser Gly Leu Thr Ser Arg Asn Tyr Phe Leu Val
180                 185                 190

AAC GGA ACC AGC CGA GAA ATT GGC ATC CAA TTC TTT GAT TCA CTT TTG        779
Asn Gly Thr Ser Arg Glu Ile Gly Ile Gln Phe Phe Asp Ser Leu Leu
195                 200                 205                 210

GAC ACA AAG AAA ATA GAA CGA TTC AAC CCT CCC AGC AAT GTC ACC GTA        827
Asp Thr Lys Lys Ile Glu Arg Phe Asn Pro Pro Ser Asn Val Thr Val
             215                 220                 225

CGT TGC AAC ACG ACG CAC TGC CTC GTA CGG TGG AAA CAG CCC AGG ACC        875
Arg Cys Asn Thr Thr His Cys Leu Val Arg Trp Lys Gln Pro Arg Thr
             230                 235                 240
```

```
TAT CAG AAG CTG TCG TAC CTG GAC TTT CAG TAC CAG CTG GAC GTC CAC       923
Tyr Gln Lys Leu Ser Tyr Leu Asp Phe Gln Tyr Gln Leu Asp Val His
            245                 250                 255

AGA AAG AAT ACC CAG CCT GGC ACG GAA AAC CTA CTG ATT AAT GTT TCT       971
Arg Lys Asn Thr Gln Pro Gly Thr Glu Asn Leu Leu Ile Asn Val Ser
260                 265                 270

GGT GAT TTG GAA AAT AGA TAC AAC TTT CCA AGC TCT GAG CCC AGA GCA      1019
Gly Asp Leu Glu Asn Arg Tyr Asn Phe Pro Ser Ser Glu Pro Arg Ala
275                 280                 285                 290

AAA CAC AGT GTG AAG ATC AGA GCT GCA GAC GTC CGC ATC TTG AAT TGG      1067
Lys His Ser Val Lys Ile Arg Ala Ala Asp Val Arg Ile Leu Asn Trp
            295                 300                 305

AGC TCC TGG AGT GAA GCC ATT GAA TTT GGT TCT GAC GAC GGG AAC CTC      1115
Ser Ser Trp Ser Glu Ala Ile Glu Phe Gly Ser Asp Asp Gly Asn Leu
            310                 315                 320

GGC TCT GTG TAC ATT TAT GTG CTC CTA ATC GTG GGA ACC CTT GTC TGT      1163
Gly Ser Val Tyr Ile Tyr Val Leu Leu Ile Val Gly Thr Leu Val Cys
            325                 330                 335

GGC ATC GTC CTC GGC TTC CTC TTT AAA AGG TTC CTT AGG ATA CAG CGG      1211
Gly Ile Val Leu Gly Phe Leu Phe Lys Arg Phe Leu Arg Ile Gln Arg
340                 345                 350

CTG TTC CCG CCA GTT CCA CAG ATC AAA GAC AAA CTG AAT GAT AAC CAT      1259
Leu Phe Pro Pro Val Pro Gln Ile Lys Asp Lys Leu Asn Asp Asn His
355                 360                 365                 370

GAG GTG GAA GAC GAG ATC ATC TGG GAG GAA TTC ACC CCA GAG GAA GGG      1307
Glu Val Glu Asp Glu Ile Ile Trp Glu Glu Phe Thr Pro Glu Glu Gly
            375                 380                 385

AAA GGC TAC CGC GAA GAG GTC TTG ACC GTG AAG GAA ATT ACC              1349
Lys Gly Tyr Arg Glu Glu Val Leu Thr Val Lys Glu Ile Thr
390                 395                 400

TGAGACCCAG AGGGTGTAGG AATGGCATGG ACATCTCCGC CTCCGCGACA CGGGGGAACT    1409

GTTTTCTTGA TGATGCTGTG AACCTTTATA TCATTTTCTA TGTTTTTATT TAAAAACATG    1469

ACATTTGGGG CCAGGCGCGG TGGCTCACGC CTGTAATCCC AGCACTTTGG GAGGCCAAGG    1529

CAGGCGGATC ACCTGAGGTC AGGAGTTCAA GACCAGCCTG CCCAACATGG TGAAACCCCA    1589

TCTGGACTAA AAATGCAGAA ATTTACCCAG GCACGGCGGC GGACGCCCAT CATCCCAGCT    1649

ACTTGGGAGG CTGAGGCAGG AGAATTGCTT GAACCCGTGA GGCGGAGGTT GTAGTGAGCC    1709

AAGATCGCAC CATTGCACAC CAACCTGCGT GACAGAGCAA GATTGCATCT CAAAACAAAC    1769

AATAATAATA AATAATAAAA ACCTGATATT TGGCTGGGA                          1808
```

(2) INFORMATION FOR SEQ ID NO:5:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:5:

```
Met Pro Trp Gly Leu Gln Gln Glu Asn Pro Trp Arg Gln Gln Ile Arg
 1               5                  10                  15

Glu Ala Ala Met Phe Ala
            20
```

(2) INFORMATION FOR SEQ ID NO:6:

(i) SEQUENCE CHARACTERISTICS:
        (A) LENGTH: 400 amino acids (B) TYPE: amino acid
(D) TOPOLOGY: linear (ii) MOLECULE TYPE: protein (xi) SEQUENCE DESCRIPTION: SEQ ID NO:6:

```
Met Leu Leu Leu Val Thr Ser Leu Leu Leu Cys Glu Leu Pro His Pro
  1               5                  10                  15

Ala Phe Leu Leu Ile Pro Glu Lys Ser Asp Leu Arg Thr Val Ala Pro
                 20                  25                  30

Ala Ser Ser Leu Asn Val Arg Phe Asp Ser Arg Thr Met Asn Leu Ser
             35                  40                  45

Trp Asp Cys Gln Glu Asn Thr Thr Phe Ser Lys Cys Phe Leu Thr Asp
         50                  55                  60

Lys Lys Asn Arg Val Val Glu Pro Arg Leu Ser Asn Asn Glu Cys Ser
 65                  70                  75                  80

Cys Thr Phe Arg Glu Ile Cys Leu His Glu Gly Val Thr Phe Glu Val
                 85                  90                  95

His Val Asn Thr Ser Gln Arg Gly Phe Gln Gln Lys Leu Leu Tyr Pro
                100                 105                 110

Asn Ser Gly Arg Glu Gly Thr Ala Ala Gln Asn Phe Ser Cys Phe Ile
            115                 120                 125

Tyr Asn Ala Asp Leu Met Asn Cys Thr Trp Ala Arg Gly Pro Thr Ala
130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
            180                 185                 190

Leu Val Asn Gly Thr Ser Arg Glu Ile Gly Ile Gln Phe Phe Asp Ser
            195                 200                 205

Leu Leu Asp Thr Lys Lys Ile Glu Arg Phe Asn Pro Pro Ser Asn Val
210                 215                 220

Thr Val Arg Cys Asn Thr Thr His Cys Leu Val Arg Trp Lys Gln Pro
225                 230                 235                 240

Arg Thr Tyr Gln Lys Leu Ser Tyr Leu Asp Phe Gln Tyr Gln Leu Asp
                245                 250                 255

Val His Arg Lys Asn Thr Gln Pro Gly Thr Glu Asn Leu Leu Ile Asn
            260                 265                 270

Val Ser Gly Asp Leu Glu Asn Arg Tyr Asn Phe Pro Ser Ser Glu Pro
            275                 280                 285

Arg Ala Lys His Ser Val Lys Ile Arg Ala Ala Asp Val Arg Ile Leu
290                 295                 300

Asn Trp Ser Ser Trp Ser Glu Ala Ile Glu Phe Gly Ser Asp Asp Gly
305                 310                 315                 320

Asn Leu Gly Ser Val Tyr Ile Tyr Val Leu Leu Ile Val Gly Thr Leu
                325                 330                 335

Val Cys Gly Ile Val Leu Gly Phe Leu Phe Lys Arg Phe Leu Arg Ile
            340                 345                 350

Gln Arg Leu Phe Pro Pro Val Pro Gln Ile Lys Asp Lys Leu Asn Asp
            355                 360                 365

Asn His Glu Val Glu Asp Glu Ile Ile Trp Glu Glu Phe Thr Pro Glu
370                 375                 380
```

```
Glu Gly Lys Gly Tyr Arg Glu Glu Val Leu Thr Val Lys Glu Ile Thr
385                 390                 395                 400
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Val Xaa Xaa Arg Xaa Xaa Trp Ser Xaa Trp Ser
1               5                   10
```

(2) INFORMATION FOR SEQ ID NO:8:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Ser Cys Phe Cys Thr Trp Cys Cys His Leu Arg Trp Val Lys Ile Arg
1               5                   10                  15

Ala Ala Asp Val Arg Ile Leu Asn Trp Ser Ser Trp Ser Leu Ile Val
                20                  25                  30

Gly Thr Leu Val Cys Gly Ile Val Leu Gly Phe
            35                  40
```

(2) INFORMATION FOR SEQ ID NO:9:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ser Cys Phe Cys Glu Trp Cys Cys Gln Leu Arg Trp Val Gln Leu Arg
1               5                   10                  15

Ala Gln Glu Glu Phe Gly Gln Gly Trp Ser Glu Trp Ser Leu Ala
                20                  25                  30

Phe Gly Thr Leu Leu Cys Ile Ala Ile Val Leu Arg Phe
            35                  40                  45
```

(2) INFORMATION FOR SEQ ID NO:10:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Leu Cys Phe Cys Phe Trp Cys Cys Ser Leu Arg Trp Val Arg Ala Arg
1               5                   10                  15
```

```
                               -continued
Met Ala Glu Pro Ser Phe Ser Gly Phe Trp Ser Ala Trp Ser
            20                  25                  30

(2) INFORMATION FOR SEQ ID NO:11:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Thr Cys Phe Cys Val Trp Cys Cys Val Trp Ser Trp Val Arg Val Lys
 1               5                  10                  15

Pro Leu Gln Gly Glu Phe Thr Thr Trp Ser Pro Trp Ser
            20                  25

(2) INFORMATION FOR SEQ ID NO:12:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Cys Phe Cys Trp Cys Cys Arg Trp Val Arg Glu Trp Ser Trp Ser Leu
 1               5                  10                  15

Gly Thr Leu Cys Ile Val Leu Phe
            20

(2) INFORMATION FOR SEQ ID NO:13:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Lys Cys Arg Cys Trp Trp Cys Cys Phe Phe Lys Trp Val Gln Thr Arg
 1               5                  10                  15

Cys Lys Pro Asp His Gly Tyr Trp Ser Arg Trp Ser
            20                  25
```